United States Patent
Sakurada

(10) Patent No.: US 10,303,845 B2
(45) Date of Patent: May 28, 2019

(54) BIOLOGICAL INFORMATION PROCESSING METHOD AND DEVICE, RECORDING MEDIUM AND PROGRAM

(75) Inventor: Kazuhiro Sakurada, Kanagawa (JP)

(73) Assignee: Sony Corporation, Tokyo (JP)

( * ) Notice: Subject to any disclaimer, the term of this patent is extended or adjusted under 35 U.S.C. 154(b) by 575 days.

(21) Appl. No.: 13/704,940

(22) PCT Filed: Jun. 28, 2011

(86) PCT No.: PCT/JP2011/064743
§ 371 (c)(1),
(2), (4) Date: Dec. 17, 2012

(87) PCT Pub. No.: WO2012/005138
PCT Pub. Date: Jan. 12, 2012

(65) Prior Publication Data
US 2013/0110409 A1    May 2, 2013

(30) Foreign Application Priority Data

Jul. 5, 2010   (JP) ................. 2010-153388
Feb. 1, 2011   (JP) ................. 2011-019632

(51) Int. Cl.
| | |
|---|---|
| G01N 33/48 | (2006.01) |
| G01N 33/50 | (2006.01) |
| G06F 19/10 | (2011.01) |
| A61B 5/145 | (2006.01) |
| A61B 5/00 | (2006.01) |
| G06F 19/24 | (2011.01) |
| G06F 19/18 | (2011.01) |

(52) U.S. Cl.
CPC ............ *G06F 19/10* (2013.01); *A61B 5/145* (2013.01); *A61B 5/14546* (2013.01); *A61B 5/7275* (2013.01); *G06F 19/24* (2013.01); *A61B 5/48* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 5,840,020 A | 11/1998 | Heinonen et al. | |
| 6,546,269 B1 | 4/2003 | Kurnik | |
| 2002/0081285 A1* | 6/2002 | Parikh ............... | A61K 38/2207 424/93.21 |
| 2003/0219764 A1 | 11/2003 | Imoto et al. | |
| 2006/0292696 A1* | 12/2006 | Noffsinger ......... | B01J 39/26 436/66 |
| 2007/0122795 A1 | 5/2007 | Shiraishi | |
| 2009/0312621 A1 | 12/2009 | Verbitskly et al. | |

FOREIGN PATENT DOCUMENTS

| | | |
|---|---|---|
| CN | 101500475 | 8/2009 |
| JP | 2003-067499 A | 3/2003 |
| JP | 2003-067499 | 7/2003 |
| JP | 2004-529630 | 9/2004 |
| JP | 2004-535612 A | 11/2004 |
| JP | 2005-516269 | 6/2005 |
| JP | 2006-517426 | 7/2006 |
| JP | 2007-052766 | 3/2007 |
| JP | 2007-079923 | 3/2007 |
| JP | 2009-517188 | 4/2009 |
| WO | 2009-120909 A1 | 10/2009 |

OTHER PUBLICATIONS

Cole et al. (Nature Genetics Supplement 1999, vol. 21 pp. 38-41).*
Neil Risch published in Jun. 2000, (Risch, N.J. Nature, Searching for genetic determinants in the new millennium, Jun. 15, 2000 vol. 405, pp. 847-856).*
(Lockhart, D.J. et al. Nature Jun. 15, 2000, vol. 405 pp. 827-836).*
(Roses, A.D. Nature, Pharmacogenetics and the practice of medicine, Jun. 15, 2000 pp. 857-865).*
Molar, E.J. et al. Physiol. Genomics, Analysis of molecular profile data using generative and discriminative methods, Dec. 2000, vol. 4 pp. 109-126).*
Romanos et al. Foreign gene expression in yeast: a review. Yeast, vol. 8, pp. 423-488. (Year: 1992).*
Chinese Office Action dated Sep. 17, 2013 for corresponding Chinese Appln. No. 201180032593.4.
Singapore Written Opinion & Search Report dated Jul. 9. 2014, for corresponding Singapore Appln. No. 2012092086.
"Crossing the Valley of Death", Nature, vol. 453, pp. 840-842, Jun. 12, 2008. (3 pages).
Kazuhiro Sakurada, "Life as Inheritance of History, System Biology from Epigenetics." (23 pages).
Ku et al., "The pursuit of genome-wide association studies: where are we now?" Journal of Human Genetics, vol. 55, pp. 195-206, 2010. (12 pages).
Kazuhiro Sakurada, "Toward Science of Human Life System," 4 H3-07 Invitation Lecture. (2 pages).
Abstract of Lecture of the Chemical Society of Japan, 2009, vol. 89, No. 2, p. 1245 (4H3:07).

(Continued)

*Primary Examiner* — Russell S Negin
(74) *Attorney, Agent, or Firm* — K&L Gates LLP

(57) ABSTRACT

Provided is a biological information processing method and a device, a recording medium and a program that are able to predict and control changes in the state of an organism. The expression level of molecules in an organism is measured over a specific time interval; the measured time-series data is divided into a periodic component, an environmental stimulus response component and a baseline component; constant regions of the time-series data are identified from variations in the baseline component or from the amplitude or periodic variations of the periodic component; and causal relation between the identified constant regions is identified. The relation between the external environment and variations in the internal environment is identified and from the identified causal relation between the constant regions, changes in the state of the organism are inferred.

31 Claims, 12 Drawing Sheets

(56) References Cited

OTHER PUBLICATIONS

Sakurada, Open System Science, from Science of Principle Clarification to Science of Problem Clarification, NTT Publication Co., Ltd., 2009, pp. 59-83.
Japanese Office Action dated Mar. 24, 2015, for corresponding Japanese Appln. No. 2011-019632.
Chinese Office Action (with English translation) dated Apr. 6, 2017 in corresponding Chinese application No. 2011800325934 (15 pages).
Japanese Office Action (with English translation) dated Apr. 13, 2017 in corresponding Japanese application No. 2015-220514 (8 pages).
Bar-Joseph, Ziv, Analyzing time series gene expression data, Bioinformatics, 2004, vol. 20, No. 16. pp. 2493-2503.
Aspiration, 2009, vol. 28, No. 3, pp. 229-235.
Extended European Search Report issued in corresponding European application No. 11803473.5, dated Aug. 29, 2016 (11 pages).
Japanese Office Action (with English translation) dated Sep. 13, 2016 in corresponding Japanese application No. 2015-220514 (12 pages).
Korean Intellectual Property Office, Notice of Preliminary Rejection issued to Korean Patent Application No. 10-2012-7033602, dated Nov. 14, 2017.
Vallee et al., "Prenatal Stress Induces High Anxiety and Postnatal Handling Induces Low Anxiety in Adult Offspring: Correlation with Stress-Induced Corticosterone Secretion," The Journal of Neuroscience, vol. 17(7), pp. 2626-2636, Apr. 1, 1997.
Japanese Office Action dated Aug. 23, 2018 in corresponding Japanese Application No. 2017-195127.
European Office Action dated Feb. 18, 2019 for European App. 11803473.5 (12 pages).
Using Bayesian Networks to Analyze Expression Data by Friedman et al.; Journal of Computational Biology, vol. 7, Nos. 3/4, 2000, Mary Ann Liebert, Inc.; pp. 601-620.
Japanese Office Action dated Mar. 28, 2019 for App. 2017-195127 (16 pages).

\* cited by examiner

BIOLOGICAL INFORMATION PROCESSING METHOD AND DEVICE, RECORDING MEDIUM AND PROGRAM

CROSS REFERENCES TO RELATED APPLICATIONS

The present application is a national stage of International Application No. PCT/JP2011/064743 filed on Jun. 28, 2011 and claims priority to Japanese Patent Application No. 2010-153388 filed on Jul. 5, 2010, and 2011-019632 filed on Feb. 1, 2011, the disclosure of which is incorporated herein by reference.

BACKGROUND

The present application relates to a biological information processing method and a device, a recording medium and a program, and particularly to a biological information processing method and a device, a recording medium and a program that predict and control future changes in the state of a human organism.

A decrease in productivity of development in a new treatment scheme, diagnostic scheme, and prevention scheme has been a significant issue in resolving a social problem associated with health. The decrease in productivity is caused since enormous perception obtained in basic biology fails to be effectively used to resolve an issue in clinical practice (Non-Patent Document 1). According to recent international research, the current world population having diabetes has increased to 285 million. The population having diabetes is expected to exceed 435 million, which is larger than the population of North America, by the year 2030. This indicates that prevalence of diabetes of adults in the world is close to 7%.

A human includes 60 trillion cells, has complexity of storing DNA (Deoxyribonucleic acid) information including 6 billion base pairs in each cell, and is a dynamic system that performs cell divisions $10^{16}$ times in the human's life. In addition to millions of base substitutions, diversity in a DNA structure such as loss, duplication, and inversion of a DNA sequence is observed between two individuals.

One of characteristics of biology is a hierarchy. A human body is based on a "cell" including molecules such as DNA or protein, and is characterized by a subsystem, a tissue, and an organ including various cells. The hierarchy diversifies a time scale of a responsive reaction with respect to a stimulus from an environment. An information propagation within a cell proceeds in a unit of millisecond or second, an information propagation between cells proceeds in a scale of a minute or an hour, and a process of a cell growth or differentiation proceeds in a unit of date and hour. The diversity of the time scale causes a time delay in an organism.

In a complex and diverse life phenomenon, basic biology has clarified a causal relation between molecules included in an organism to represent an organism as a mechanical system. This is implemented by a scheme of selecting a particular molecular parameter from among a plurality of parameters, and changing the particular molecular parameter.

In a clinical science, disease is treated by emphasizing alleviation of associated symptoms.

In addition, to obtain a clinical effect, an experimental rule such as a relational expression and a rule between an intervention such as dosing and a clinical outcome is inferred from a biological index in a specified time.

A significant objective in modern medicine is to provide appropriate health management or treatment to each individual. When a treatment scheme or medication of which safety and efficacy have been statistically verified is marketed and used by a large-scale group, a side effect or no efficacy is observed in a portion of patients. One of the causes thereof is genetic diversity of a patient receiving treatment. With regard to a difference in disease onset rate due to genetic diversity, an analysis has been recently in progress by "(Genome wide association study; GWAS)" (Non-Patent Document 2).

CITATION LIST

Non-Patent Document

Non Patent Document 1: Nature 453; 840-9, 2008
Non Patent Document 2: J. Hum. Genet. Doi: 10.1038/jhg.2010.19

SUMMARY

Problems to be Solved by the Invention

However, in a current clinical practice, to measure a limited biological index only in a limited time, and statistically average the index, various characteristics acquired by various people included in a group over time are abstracted accordingly. In addition, as opposed to basic biology emphasizing a micro-scale issue, clinical research handles, as a clinical outcome, a macro-scale issue of an individual level such as a physical disability, a loss of a physiological function, and a particular illness or body condition. In basic biology and clinical research, a gap is included between levels.

In addition, a current treatment strategy is forced to construct a disease by abstracting diversification acquired over time, and thus every treatment strategy is a symptomatic therapy. However, an original health state may not be recovered from a disease by alleviating a symptom.

These issues indicate that a concept of a current basic biology or clinical practice may not predict and control a future change in a human biological state, making it difficult to develop an effective prevention scheme and treatment scheme.

The present application has been contrived in view of the above circumstances, and may predict and control a future change in a human biological state.

Solutions to Problems

An aspect of the technology is a biological information processing method including the steps of: measuring an expression level of molecules in an organism over a specific time interval; dividing measured time-series data into a periodic component, an environmental stimulus response component and a baseline component; identifying constant regions of the time-series data from variations in the baseline component or from the amplitude or periodic variations of the periodic component, and identifying causal relation between the identified constant regions; and inferring changes in the state of the organism from the identified causal relation between the constant regions.

The identifying step may further identify the relation between changes in the state of the organism and the external environment, and the inferring step may further infer disease onset in the organism from the identified relation between changes in the state of the organism and the external environment.

The measuring step may measure the molecules representing a general state, a local state, and a chromosome state.

The molecules may be blood molecules of the organism.

The molecules may be molecules associated with metabolic syndrome.

The molecules may be molecules in a culture medium.

According to an aspect of the technology, an expression level of molecules in an organism is measured over a specific time interval, measured time-series data is divided into a periodic component, an environmental stimulus response component and a baseline component, constant regions of the time-series data are identified from variations in the baseline component or from the amplitude or periodic variations of the periodic component, and causal relation between the identified constant regions is identified. Changes in the state of the organism are inferred from the identified causal relation between the constant regions.

A biological information processing device, a recording medium, and a program of the aspect of the technology are a biological information processing device, a recording medium, and a program corresponding to the biological information processing method of the aspect of the technology described above.

Another aspect of the technology is a biological information processing method including the steps of: acquiring cell memory information of a biological molecule of an organism of a subject; acquiring environmental information associated with an environmental condition of the organism of the subject; acquiring gene information associated with a gene sequence included in the organism of the subject; and searching for similar information of an organism of a person other than the subject associated with the acquired cell memory information, environmental information, and gene information.

The gene information may be a single nucleotide polymorphism and a structural polymorphism.

The searching may be performed based on similarity in a correlation among the cell memory information, the environmental information, and the gene information.

The step of acquiring cell memory information includes the steps of: measuring an expression level of molecules in an organism of the subject over a specific time interval; dividing measured time-series data into a periodic component, an environmental stimulus response component and a baseline component; and identifying constant regions of the time-series data from variations in the baseline component or from the amplitude or periodic variations of the periodic component, and identifying causal relation between the identified constant regions.

According to the other aspect of the technology, cell memory information of a biological molecule of an organism of a subject is acquired, environmental information associated with an environmental condition of an organism of the subject is acquired, gene information associated with a gene sequence included in an organism of the subject is acquired, and similar information of an organism of a person other than the subject associated with the acquired cell memory information, environmental information, and gene information is searched for.

A biological information processing device, a recording medium, and a program of the other aspect of the technology are a biological information processing device, a recording medium, and a program corresponding to the biological information processing method of the other aspect of the technology described above.

Effects of the Invention

As described above, according to an aspect and another aspect of the technology, it is possible to predict and control future changes in the state of a human organism.

Additional features and advantages are described herein, and will be apparent from the following Detailed Description and the figures.

DETAILED DESCRIPTION

Figure 1:
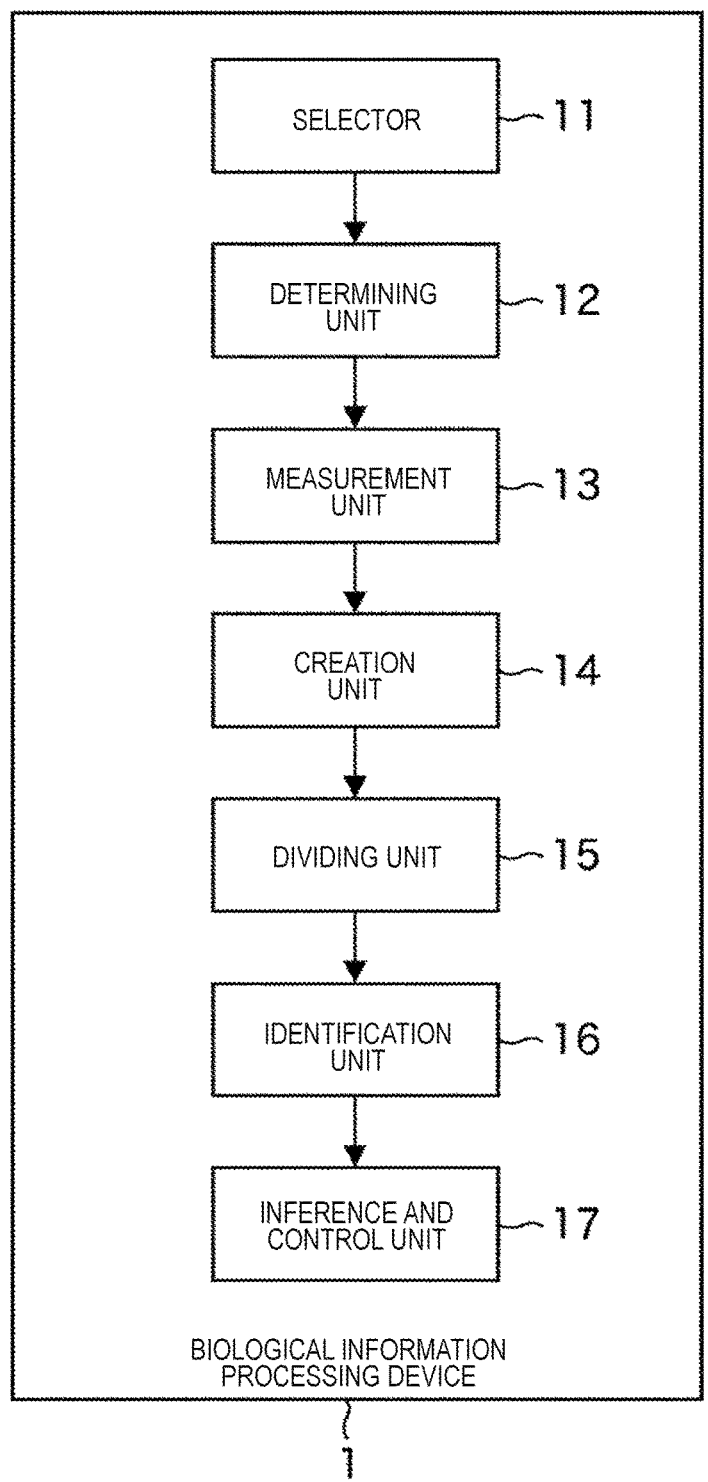
FIG. 1 is a block diagram illustrating a configuration of an embodiment of a biological information processing device.

Hereinafter, a mode (hereinafter, referred to as an embodiment) for carrying out the technology will be described. Description will be made in the following order.

1. Progress
2. Definition
3. First embodiment
4. Second embodiment
5. Third embodiment
6. Fourth embodiment
7. Fifth embodiment
8. Sixth embodiment
9. Seventh embodiment
10. Eighth embodiment
11. Ninth embodiment <Progress>

First, a progress of the technology will be described as follows.

Developers of the technology have closely examined a method of representing a time evolution of a human organism and predicting and controlling a direction of change of the future. As a result, in addition to three parameters of a genetic type, a phenotype, an external environment conventionally used to formulate a life, by introducing a new parameter referred to as a "cell memory undergoing a time evolution," it is found that a problem of a human organism undergoing a time evolution may be resolved. In addition, to formulate the "cell memory undergoing a time evolution," the developers of the technology have noted that a cell memory of a transcription factor having a property of a bistable switch expressed in each cell changes over time due to epigenetic modification and genetic modification. The epigenetic modification includes DNA methylation or histone modification, and the genetic modification includes a DNA mutation or a structural change.

The developers of the technology have constructed the "cell memory model undergoing a time evolution" which indicates that genetic modification and epigenetic modification change a cellular state by altering an expression level of a target gene product controlled by a bistable switch. Further, according to the "cell memory model undergoing a time evolution," the developers of the technology have constructed a concept referred to as a "chromosome state" including a transcription factor that functions in a chromosome, genetic modification, and epigenetic modification.

Next, to estimate the "chromosome state" from an observed value of a general state or a local state, the developers of the technology have linked the generate state, the local state, and the "chromosome state" which are three different levels constituting a human organism system to one another. For this, the developers of the technology have constructed a macro model, a meso model, and a micro model corresponding to each level of the general state, the local state, and the "chromosome state." Further, using this "organism level link model," the developers of the technology propose a method of linking and formulating the macro model, the meso model, and the micro model in units of cells.

Next, to observe the "chromosome state" that manages a time evolution of a human organism, the developers of the technology have examined development of a method of integrating the "organism level link model" into a time-series model, and found a new integration method using a "biological state space model." Then, the developers of the technology propose a method of extracting the "chromosome state" by dividing time-series data of a molecular marker that reflects the general state using the "biological state space model" into a periodic component, an environmental stimulus response component, and a baseline component.

Next, the developers of the technology have closely examined development of a control model using data of the time evolutional change of a human organism that can be represented by the technology for the first time. Then, the developers of the technology find a concept of a "constructed change" indicating that an initial input from an external environment changes responsiveness to a subsequent input from the external environment, and propose a "dynamic construction model" in which the "cell memory undergoing a time evolution" is controlled by the "constructed change."

In addition, the developers of the technology have conducted a close examination to apply the "dynamic construction model" to an issue in clinical practice, and proposed a method of an "organism local constant region model" for identifying a constant region of time-series data associated with an expression level of a molecule produced in an organism using the "biological state space model." Furthermore, the developers of the technology propose a method of analyzing a causal structure and a biological state tracking using, as a node, an organism local constant region found during a time series variation of an expression level of a molecule produced in an organism.

Definition

Next, definition of terms used in description of embodiments of the technology will be described.

A time evolution of a human organism indicates a process in which a state or a function of a human organism irreversibly changes over time. A human dies after undergoing irreversible changes such as generation, birth, growth, and aging from a moment of fertilization. An onset of a disease progresses to a previous step of the onset receiving a potential change, the onset, a particular disordered physiological function, a loss of a particular physiological function, a physical disability, and a death. This indicates that an instant in a human organism and the time of another instant are not homogeneous.

The "cell memory undergoing a time evolution" indicates that a cell memory constructed by a transcription factor is changed by genetic modification and epigenetic modification introduced as an environmental input to a cell or a result from an accident. A cell memory has conventionally been defined as a phenomenon in which a change in state of a cell acquired by a stimulus from an external environment is maintained even after the stimulus from the external environment disappears (Cell 140: 13-18, 2010). A cellular state is represented by a type, an amount, and a modification property of a molecule expressed in a cell, and a maintenance and a change of the cellular state is controlled by a transcription factor.

That is, a conventional cell memory provides a concept that a state of a cell provides a particular equilibrium by a characteristic of a bistable switch included in a transcription factor. However, only the uniform time of ON and OFF of a switch may be provided. However, actually, genetic modification and epigenetic modification introduced over time change a cellular state provided by a transcription factor over time, thereby further diversifying a state of a cell when compared to the cellular state assumed only by a transcription factor.

That is, in the "cell memory undergoing a time evolution," a diversity of a cellular state may be formulated by a history that may be inherited such as genetic modification and epigenetic modification, and the "cell memory undergoing a time evolution" is essentially different from a conventional cell memory in that the non-uniform time may be managed.

A transcription factor forms a molecular base of a conventional cell memory. When a circuit of a transcription factor is nonlinear and indicates a bistable characteristic, a state of a molecule is in equilibrium of ON or OFF, and the memory is inherited even after a cell division. An affinity formed between a transcription factor and a binding site of a promoter, and cooperativeness or multimerization among a plurality of transcription factors provide a characteristic of a nonlinearity to a transcription factor.

The nonlinearity resists a transient disturbance and causes an expression level to be inherited by providing a threshold-like characteristic to a response of a transcription factor. In addition, a transcription factor acquiring a sufficiently great Hill coefficient by a positive feedback or a positive or negative dual feedback acquires a characteristic of a bistable switch, and a change in state is locked even after an original input disappears. That is, a type, an amount, and a post-translational modification of a transcription factor expressed in a cell forms a skeleton of a conventional cell memory.

Genetic modification such as a single nucleotide polymorphism observed in a human genome, a defect, a duplication, and a change in the number of copies of a portion of a DNA sequence, and epigenetic modification such as DNA methylation, histone modification, and a protein denaturation manage a molecular base of the "cell memory undergoing a time evolution" (Nature Review Genetics 7: 85-97, 2006, Cell 128: 655-658, 2007).

Each of genetic modification and epigenetic modification directly or indirectly changes a parameter associated with a characteristic of nonlinearity or a bistable switch of a transcription factor, thereby modifying a function of a conventional cell memory.

As for genetic modification, a relation between a single nucleotide polymorphism and a disease onset rate is analyzed by a genome-wide linkage analysis scheme. Using the analysis scheme, nineteen genes have been identified as a related gene of type 2 diabetes. However, only 1% of the total is diabetic patients having a mutant (Nature 462: 307-314, 2009). Similarly, a BRCA 1/2 gene mutation is observed in only 3% of the entire breast cancer patients. In an experiment comparing a lifespan of identical twins to a lifespan of non-identical twins, an epidemiologic investigation indicates that a percentage of contribution to a lifespan by a gene sequence is about 15% to 25% (Hum. Genet 97: 319-323, 1996).

Epigenetic modification is defined as an alteration of a gene function that may be inherited without entailing a change in a DNA sequence. DNA methylation and chemical modification of a chromatin protein are a molecular substance of epigenetics. In addition, an alteration of a cell function due to denaturation of protein such as prion protein and amyloid protein is classified as epigenetics in a broad sense. A concept of epigenetics was proposed by Waddington to describe a mechanism in which genetic information is changed to a phenotype in a process of generation.

However, a function of epigenetics affects establishment and maintenance of a tissue or a cell-specific genetic expression. In addition to this, a stimulus due to nutritive conditions, a social stress, and chemical substances introduces epigenetic modification. It has been reported by an epidemiological research of humans that a stimulus from an environment received during the stage of an unborn baby or a newborn baby affects an onset rate of a chronic disease in adulthood through epigenetics (Stem Cell Res. 4; 157-164, 2010).

The above-described epigenetic modification is referred to as environmental epigenetics to be distinguished from development-type epigenetics associated with cell differentiation. The developers of the technology have found that a function of environmental epigenetics is regarded as a "function of updating DNA information based on a change in external environment information."

A scale of the time to be inherited is different between genetic modification and epigenetic modification affecting alteration of a function of a transcription factor. Genetic modification is a primary cause of a cell memory inherited from parents to a child. On the other hand, epigenetic modification performs a primary function as a cell memory acquired in a generation.

However, a discovery of transgenerational epigenetics indicates that environmental epigenetics introduced in a germ line resists an initialization of generation, and is inherited from parents to a child (Stem Cell Res. 4; 157-164, 2010). In addition, new genetic modification such as a DNA mutation or transposition introduced in a somatic cell is regarded as a primary cause of carcinogenesis.

A "model of a cell memory undergoing a time evolution" is a new concept introduced to formulate the "cell memory undergoing a time evolution" that changes over time due to genetic modification and epigenetic modification. An expression signature of a transcription factor, genetic modification, and epigenetic modification that change over time are integrated into a "chromosome state."

This is different from a conventional cell memory which defines only two states of ON and OFF with respect to a transcription factor. In a chromosome state of the technology, an inhibitory effect and an induction with respect to a target gene product by a transcription factor discretely change. By introducing a concept of the chromosome state, a cellular state is formulated as a connection of two time series variations of the chromosome state and an external environmental state of a cell. Further, the "cell memory undergoing a time evolution" is formulated as a function of a time series variation of the "chromosome state."

An "organism level link model" is a new model proposed for a connection of the "chromosome state" and an "individual state" requested to use the "cell memory undergoing a time evolution" for a prediction of a health or a disease of an individual level. A human individual is a continuum hierarchically put in order. A cell is formed from molecules, and a further complex entity such as a tissue and an organ is constructed on cells. A state of a human body may be classified into a general state, a local state, and a chromosome state based on the above-described hierarchical structure, and a model of three different scales of macro, meso, and micro may be constructed in response to each state.

A macro model is a model regarding an entire body as a state. Thus, the state may be defined by an expression signature of a molecule diffusing in the entire body. Representative examples of the molecule diffusing in the entire body include a hormone of an endocrine system or an immune system, a growth factor, and a cytokine. In addition, adrenaline and noradrenaline affecting a control of an autonomic nervous system defines a state of an entire body.

A meso model is a model that discovers a state of a homogeneous local space within an organism. Each organ or tissue forms a homogeneous state as a unity. In general, a symptom of an inflammation and the like specifically occurs in a local site. This includes multiple cells forming an inflamed site. On the other hand, a rejuvenescence of a tissue is controlled by propagation and differentiation of a few tissue stem cells. As such, the meso model includes the different number or type of cells such as one cell, an inflamed tissue, a tissue, and an organ. The local state is defined by systematic molecules in addition to an autocrine and paracrine molecular group expressed within a local environment.

A micro model is a model that discovers a state of a chromosome included in each cell. A reason why the micro model is not in a cellular state is that a cellular state only represents an overt cell memory driven by a transcription factor, and a potential change including genetic modification or epigenetic modification is abstracted. A chromosome state is defined by genetic modification, an epigenetic modification characteristic, and an expression signature of a transcription factor.

Epigenetic modification and an expression signature of a transcription factor in a state of a chromosome are controlled by a local environment and a systematic environment of a cell having the chromosome. A cell that produces systematic molecules is also controlled by a local state of a cell and a chromosome state in addition to a general state, and a cell that produces an autocrine and paracrine factor which is a molecule of a local environment is controlled by the general state, the local environment of the cell, and the chromosome state. That is, it is clear from an analysis that it is formulated that the "chromosome state," the local state, and the general state concurrently determine a change of one another, are concurrently directed, and concurrently undergo a time evolution. The formulation is referred to as an "organism level link model."

A human receives stimuli from various different environments depending on a social environment, a behavioral characteristic of the human, and the like. A stimulus from external environments is recognized by various systems of a somatic cell, and is translated into an internal environment change of a human body. Therefore, due to individual differences of a somatic cell system receiving a stimulus, a stimulus from the same environment may not necessarily induce the same change of an internal environment. This indicates that a quantitative measurement of an environmental factor alone may fail to accurately predict a change in state of a human body. A stimulus from an environment may be classified, according to a characteristic, into a physical stress (temperature, oxygen, ultraviolet ray, and the like), a chemical stress (endocrine disruptor, carcinogen, and the like), a psychosocial stress, an exercise stress, a nourishment stress (excessive eating and starvation), an infection stress, a wound stress, and the like.

A stimulus from an environment is detected by a reception system, and then is translated into a change of a general state, a local state, and a "chromosome state" with different time delays. As such, to expand the "cell memory undergoing a time evolution" to a memory of an entire body level, time needs to be regarded as a discrete distribution rather than as a continuous distribution. Instability of a time delay is controlled by a feedback system within an organism. Accordingly, when a change in state may be discovered in a time unit in which a change from a feedback system to a new feedback system may be discovered, a problem of a time delay may be abstracted.

A "biological state space model" is a new model proposed to apply the "organism level link model" to a time-series model. Various models used for a time-series model may be generally managed in a unified manner by a state space model (Chapters 9, 11, and 12, Iwanami bookstore, Kitagawa Genshiro, Introduction to time series analysis). In addition, a large number of problems of a time series analysis are formulated as a problem of a state estimation of the state space model.

The state space model includes two submodels of a system model (x) and an observation model (y), and two interpretations are possible. When the observation model is regarded as a regression model that expresses a structure in which observed time-series data yn is observed, a state xn of the system model (x) is a regression constant. In this case, the system model is a model that expresses a state of a temporal change in a regression coefficient. On the other hand, when the state xn is regarded as a signal to be estimated, the system model represents a model that indicates a generating mechanism of a signal, and the observation model represents a state in which the signal is converted and noise is added when the signal is actually observed.

In a "dynamic construction model," xn expresses a state of an actual human body, yn is assumed to be a multivariate time-series vector associated with a measurable expression level of an extracellular factor group, and the state xn is regarded as a signal to be estimated. When the "organism level link model" is applied to a clinical prediction, it is not realistic to measure all of the "chromosome state" and the local state. However, an extracellular factor that circulates in an entire body such as a hormone, a growth factor, and a cytokine may be measured.

The "organism level link model" clarifies that the "chromosome state," the local state, and the general state concurrently determine a change of one another, are concurrently directed, and substantially undergo a co-time evolution. This indicates that data of a time series variation of an extracellular factor that circulates in an entire body contains a change of the "chromosome state" and the local state. That is, components of the local state and the "chromosome state" are directly or indirectly reflected on yn which is multivariate time-series data including a systematic blood factor of a human body state xn. This formulation scheme is referred to as the "biological state space model."

Time-series data yn of an extracellular factor that circulates in an entire body may be decomposed into a periodic component using a seasonal adjustment model, an environmental stimulus response component using a multi-linear model, and a baseline component using a polynomial smoothing spline model, respectively. A cell memory is reflected on an amplitude and a frequency of a periodic component associated with an expression of a molecule produced in an organism, a maximum expression level of a stimulus response component, and a change of a long-term baseline. Accordingly, by combining the "organism level link model" with the "biological state space model," it is possible to represent the "cell memory undergoing a time evolution" specifically and in chronological order.

The "dynamic construction model" is a control theory with respect to a human organism undergoing a time evolution. One of functions of a time evolution of an organism is that an initial stimulus from an environment changes responsiveness to a subsequent stimulus of a similar type. A molecular entity of the responsiveness change is referred to as a "constructed change" in this specification. A human organism undergoing a time evolution may be controlled by this formulation.

In the "constructed change," a representation "when stress that is not fatal to an organism is applied, responsiveness to a subsequent strong stress is improved" is generally referred to as a hormesis (Toxicology and Applied Pharmacology 222: 122-128, 2007). Up until now, a molecular mechanism of a hormesis is not clear. In a "cell memory model undergoing a time evolution" of the technology, the "constructed change" including a hormesis clarifies that a dynamic cell memory subjected to genetic modification and epigenetic modification manages a molecular basis. In this way, it may be understood that an onset of a chronic disease is caused by a mismatch between the "cell memory undergoing a time evolution" of the technology and a subsequent stress.

The "constructed change" is different from a conventional control model such as a dynamic equilibrium model and a dynamic nonequilibrium model assuming a fixed genetic algorithm based on a genetic determinism. That is, the "constructed change" assumes that a function of a gene changes due to an input from an environment or an accidental factor, and a genetically defined algorithm changes when a portion of the change is inherited to the future. Accordingly, a new control theory is needed for the "constructed change."

In the genetic determinism, a time change of a phenotype (P(t)) is expressed by a product of a given genetic type (Gx) and an environmental factor (E(t)) that changes over time, which is as follows.

$$P(t) = Gx \times E(t) \tag{1}$$

For one "constructed change," a time change of a phenotype (P(t)) is expressed by a product of a chromosome state (C(t)) that changes over time and incorporates the "cell memory undergoing a time evolution" of the technology, and an environmental factor (E(t)) that changes over time, which is as follows.

$$P(t)=C(t) \times E(t) \quad (2)$$

An organism model represented by Equation (2) is referred to as the "dynamic construction model."

An "organism local constant model" is a new data processing scheme for controlling a health and a disease using the "dynamic construction model" of the technology. Time-series data associated with an expression level of a molecule produced in an organism is generally non-stationary. However, even non-stationary data may be assumed to be stationary data in respective short intervals by dividing a time interval into appropriate short intervals. Time-series model in which a time interval is divided into appropriate short intervals by a calculation independently from the above-described system function, and respective short intervals may be assumed to be stationary is generally referred to as a local constant model (Chapter 8, Iwanami bookstore, Kitagawa Genshiro, Introduction to time series analysis).

In the "organism local constant model," to allocate changes in state of a cell memory as respective different stationary states, time-series data of an expression level change of a molecule expressed in a cell within an organism or a cultured cell is first decomposed into a periodic component, an environmental stimulus response component, and a trend component of a baseline by using the "biological state space model," and then a local constant region is identified. A cell memory influences a change of a baseline component, an amplitude and a frequency of a periodic component, and a maximum expression level and a minimum expression level of an environmental stimulus response component. Among these, three categories of a change of a baseline component, and an amplitude and a frequency of a periodic component may be identified independently from a strength of an input from an environment.

In the "organism local constant model," a local constant region is identified by the three categories. In general, the local constant region is classified into three states of an original stationary state, a new stationary state, and a change from the original stationary state to the new stationary state. The "organism local constant model" of the technology is fundamentally different from a conventional local constant model in that a constant region is specified based on a characteristic of an organism rather than simply and mechanically decomposing a time series variation into constant regions.

A "scheme of analyzing a causal structure and a biological state tracking using a local constant region as a node" is a scheme of predicting and controlling health maintenance and a disease onset by identifying an internal cause of inducing a change in state to a human organism undergoing a time evolution. A disease starts from an asymptomatic stage acquiring a potential change, and undergoes a non-stationary time evolution of acute symptoms, chronicity, a partially disordered physiological function, a partial loss of a physiological function, a physical disability, being bedridden, and a death. That is, a time evolution of a disease may be approximated to a continuous evolution of a time division regarded as a stationary state.

To predict and control a change in state of a health state or a disease, a local constant state region of a disease indicating a systematically complex aspect first needs to be coded using a molecule produced from a cell as a proxy index. This indicates that time-series data of a molecule expressed from a cell of an organ, a tissue, and a subsystem associated with a disease is divided from a viewpoint of a local constant region, and is associated with a phenotype of the disease. Using a causal structure model constructed by a biological knowledge as a prior probability, data of a time series variation of an expression level of a molecule within an organism is analyzed from multiple individuals by Bayes' approach, and an optimum type of molecule effective for the association may be selected. Accordingly, a blood molecule among various molecules produced from a cell may relatively easily acquire time-series data using a blood sample, and is effective for application of the "dynamic construction model" of the technology.

As a device for measuring a blood molecule, a glucose meter is regarded as a prototype device (Freestyle lite, Abbott Corporation). The glucose meter may measure an amount of blood glucose from a small amount of blood collected using a needle. This system may be applied to a measurement of a blood molecule other than glucose. On the other hand, recently, a scheme of percutaneously measuring a blood molecule is developed.

A time division of a constant region extracted from a time series variation of an expression level of a blood molecule is not only effective for coding a state associated with various diseases, and tracing the change in state, but also may be used to analyze a causal relation which is a cause of a disease onset. An issue of a health management is identifying a change of a blood molecule which is a cause of moving to an asymptomatic initial disease stage from a health state, and using the change for preventing an onset of a disease. In addition, an issue of a disease management is identifying a change of a blood molecule which is a cause of inducing an initial disease to a complication, and using the change for preventing an onset of the complication.

To perform a control using the "dynamic construction model" of the technology, a causal relation between changes of an expression level of a molecular group within an organism is first modeled using biological knowledge. Then, it is used to construct a graph structure associated with a probability structure/causal structure between nodes identified by extracting a constant region from data of a time series variation of a molecule within an organism of a plurality of patients. Thereafter, it is upgraded to an optimal graph structure using time-series data of a change of expression of a biological molecule of a plurality of healthy individuals or patients. A change of a graph structure may be solved as a selection problem of a covariance in regression analysis. A constructed optimum graph structure may be used to predict and control a change of a biological state of the future intended for a health management or a disease management of each individual by continuing a serial measurement of a change of expression of a biological molecule.

First Embodiment

[Application of Dynamic Construction Model to Prediction and Control of Health State and Disease State]

It is an important challenge desired from modern medicine to develop an effective prophylaxis for diabetes, cancer, immunity disorder, dementia, and cardiovascular disease based on diversity of individuals and various histories of the past. Using a "dynamic construction model" of the technology, an individual prevention may be performed for the disease group.

FIG. 1 is a block diagram illustrating a configuration of a biological information processing device 1 that predicts and controls a health state. The biological information processing device 1 includes a selector 11, a determining unit 12, a measurement unit 13, a creation unit 14, a dividing unit 15, an identification unit 16, and an inference and control unit 17.

The selector 11 selects measurement molecules. The determining unit 12 determines a molecule measurement interval. The measurement unit 13 performs a measurement. The creation unit 14 creates a graph. The dividing unit 15 divides components. The identification unit 16 identifies a constant region and a causal relation, and identifies a causal relation of molecular markers and a relation with an external environment. The inference and control unit 17 infers and controls change in states.

Figure 2:
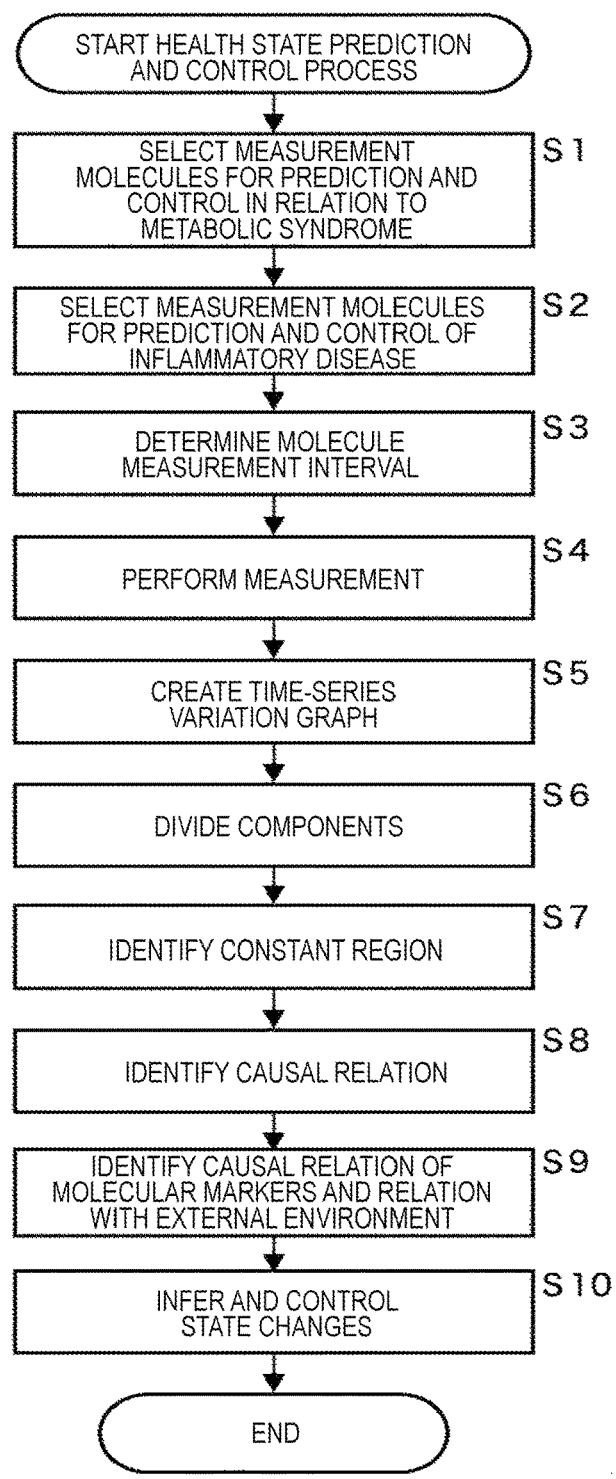
FIG. 2 is a flowchart illustrating a health state prediction and control process.

FIG. 2 is a flowchart illustrating a process of predicting and controlling a health state. Hereinafter, a prediction and control process performed by the biological information processing device 1 of FIG. 1 will be described with reference to FIG. 2.

In step S1, the selector 11 selects measurement molecules for prediction and control in relation to metabolic syndrome. That is, a type of blood molecule performing a measurement of an expression level is selected.

The "dynamic construction model" of the technology may be applied to prediction and control of an onset of a series of diseases developing from metabolic syndrome to a circulatory system disease. Diabetes is positioned among the series of diseases developing from metabolic syndrome to a circulatory system disease (Nature 444; 839-888, 2006). A metabolic disease causes obesity, visceral obesity, hyposecretion of adiponectin, insulin resistance, and the like from a problem of a lifestyle including poor eating habits and lack of exercise. Thereafter, a disease state proceeds to high blood pressure, postprandial hyperglycemia, and dyslipidemia. A state so far is referred to as metabolic syndrome.

Metabolic syndrome induces an inflammation in visceral fat, activates a regenerating system of various organs, and increases oxidant stress. As a result, a fatty liver or nonalcoholic steatohepatitis is caused. Thereafter, pancreatic dysfunction and insulin hyposecretion occur, causing an onset of diabetes.

Diabetes induces nephropathy, retinopathy, psychoneurosis, arteriosclerosis obliterans, cerebral vascular disturbance, and an ischemic cardiac disease, and proceeds to kidney dialysis, blindness, lower limb amputation, stroke, dementia, and cardiac insufficiency, resulting in death. In particular, an inflammation induced by metabolic syndrome causes cancer or a degenerative neurological disorder. When the "dynamic construction model" of the technology is applied to obesity or type 2 diabetes, a systematic blood factor below may be used as a molecular marker to use time-series data of an expression level (Nature 444; 839-888, 2006).

First, a molecular group associated with an interaction between a fat tissue and hypothalamic pituitary performs an important function for eating, glycometabolism, lipid preservation, and energy balance, and thus may be used to represent and analyze a state of poor eating and lack of exercise. For example, a chronic social stress has an epigenetic influence on an interaction between a fat tissue and a hypothalamic-pituitary-adrenal system, and changes a production of glucocorticoid and aldosterone from an adrenal gland. As a result, a function of appetite or sleep is changed.

To identify the change, it is useful to measure a time series variation of an expression level of leptin, adiponectin, visfatin, and omentin produced from a fat tissue, and ACTH produced from a pituitary in addition to glucocorticoid and aldosterone in the blood. To represent and control obesity, visceral obesity, hyposecretion of adiponectin, and insulin resistance, it is useful to measure a time series variation of an expression level of insulin, glucagon, amylin, and GLP produced from a pancreas, and lecithin and RBP4 produced from a fat tissue. In a progress from metabolic syndrome to an inflammation in visceral fat, it is useful to measure a time series variation of an expression level of TNF-α, IL-6, and MCP1 produced from a immunocyte or a fat tissue, and CRP, PAI-1, NEFA, VLDL, and LDL-ox produced from a liver.

In step S2, the selector 11 selects measurement molecules for prediction and control in relation to an inflammatory disease.

An immunity disorder including a connective tissue disease, colitis ulcerosa, and disseminated sclerosis represented by systemic lupus erythematosus (SLE) and rheumatism is also known to develop due to an infection history of the past, a characteristic of bacteria in intestines, and the like. It is useful for prediction and control of an immune system disease to track, as a molecular marker, a characteristic change of cytokine produced from a granulocyte, a monocyte, a macrophage, a dendritic cell, and a natural killer cell affecting natural immunity, and a T cell, a helper T cell (TH0, TH1, and TH2), a CD8+ positive T cell, a regulatory T cell, and a B cell affecting acquired immunity. Examples of cytokine include interleukin, interferon, chemokine, a growth factor, and a lymphotoxin factor.

In step S3, the determining unit 12 determines a molecule measurement interval.

It is preferable that a time interval for measuring an expression level of a molecular marker be short. However, time-series data of a long interval such as day, week, and month may be used depending on a measurement environment. A lot of molecules undergo a change of an expression level on a circadian rhythm of a 24 hour interval. Thus, when a measurement is performed at a time interval more than a day, data is needed to be acquired by setting a predetermined time period within a day. It is preferable that the acquired time-series data be analyzed using approximately 100 pieces of discrete data as a set regardless of a time interval at which the data is acquired. As such, to expect accuracy, a measurement is desired to be performed at least twice to three times a day, preferably 50 times to 100 times a day.

In step S4, the measurement unit 13 performs a measurement. Herein, an expression level of a blood molecule as a biological molecule is measured. Specifically, a molecule representing a general state, a local state, and a chromosome state is measured. The measurement is performed at an interval determined in step S3.

A needle may be used as a device for measuring a molecular marker in the blood. A small amount of blood may be collected using the needle. In addition, depending on molecules, a scheme of percutaneously measuring a blood molecule may be used. A type or amount of molecule may be implemented by fluorescently-labeling a selective antibody with respect to a molecule to be measured.

In step S5, the creation unit 14 creates a time-series variation graph. Specifically, a graph based on Equation (5) to Equation (11) below is created. In addition, in step S6, the dividing unit 15 divides components. That is, three components are extracted from time-series data using a biological state space model. The three components may be set to, for example, a periodic component, an environmental stimulus response component, and a baseline component.

Information used for prediction and control needs to be selected from time-series measurement data of a molecular marker. As a scheme, multivariate time-series data including a plurality of blood molecules is desired to be managed in a unified manner as a "state space model." The "state space model" includes two submodels of a system model and an observation model. In general, the two submodels are expressed using a conditional probability as follows.

$$x_n \sim q(x_n|x_{n-1}) \quad (3) \text{ (system model)}$$

$$y_n \sim r(y_n|x_n) \quad (4) \text{ (observation model)}$$

Herein, $y_n$ denotes an observed time series of a multivariable, $x_n$ denotes a k-dimensional vector that may not be directly measured, and q and r denote a conditional distribution of $x_n$ given by $x_{n-1}$ and of $y_n$ given by $x_n$, respectively. In the "biological state space model" of the technology, $x_n$ expresses a state of an actual human body, and $y_n$ indicates an expression level of a blood molecule that may be measured. When a distribution of an initial state vector $x_0$ is disposed by $P(x_0|y_0)$, a prediction of a state of a disease is an evaluation of $P(x_n|y_n)$, that is, obtaining a distribution of $x_n$ given by an observed value $y_n$ and an initial distribution.

Time-series data y(t) of respective measurable blood molecules such as a molecular group that may be used to represent a process from metabolic syndrome to diabetes, and a circulatory system disease, a molecular group associated with an immune system disease, a molecular group of an endocrine system, and the like is expressed by the following Equation. That is, it is expressible using a model including three different components.

$$y(t)=s(t)+x(t)+b(t)+v(t) \quad (5)$$

s(t): periodic component
x(t): environmental stimulus response component
b(t): baseline component
v(t): observational error An environmental stimulus response component x(t) may be formulated as a multilinear model as follows.

$$x(t)=F(t)x(t-1)+v_x(t) \quad (6)$$

i=1, 2, 3, . . . , n

In the above Equation, F(t) indicates a conversion function of an output with respect to an environmental stimulus, and $v_x(t)$ indicates a change of an environmental stimulus. Regarding a parameter of the conversion function, an optimum value is selected by applying a Yule-Walker scheme, a least square scheme, or PARCO scheme to an autoregression model.

A baseline component b(t) may be defined as below as a regression model of degree m by a polynomial smoothing spline model.

[Equation 1]

$$b(t) = \sum_{i=1}^{m} a_i b(t-i) + \varepsilon(t) \quad (7)$$

$a_i$ denotes a regression coefficient, and $\varepsilon(t)$ denotes a noise component.

Further, the baseline component b(t) may be expressed as follows.

$$b(t)=H(t,t-1)b(t-1)+V(t,t-1) \quad (8)$$

H(t, t-1) is an m×m matrix, and V(t, t-1) is a matrix associated with m-dimensional noise. An optimum function for smoothing a baseline is selected using this model.

In the "dynamic construction model" of the technology, a main component factor of the periodic component s(t) is a circadian rhythm of a 24 hour interval. When p observed values are obtained during an interval, the periodic component approximately satisfies the following Equation.

$$s(t)=s(t-p) \quad (9)$$

When this is expressed using a time delay operator G, the following Equation is approximately satisfied.

$$(1-Gp)s(t)=0 \quad (10)$$

As such, a periodic component of degree 1 may be formulated as a seasonal adjustment model as below by white noise v(t).

[Equation 2]

$$\left(\sum_{i=0}^{p-1} G^i\right)' s(t) = v(t2) \quad (11)$$

Through this processing, time-series data of a blood molecule may be divided into a periodic component, an environmental stimulus response component, and a baseline component.

In step S7, the identification unit 16 identifies a constant region. That is, a constant region is identified using the "organism local constant model."

A local constant region may be discovered by analyzing time-series data using a model of a periodic component, an environmental stimulus response component, and a baseline component. In the "dynamic construction model," it is useful to emphasize a change of a stationary state caused by the "cell memory undergoing a time evolution," and an acquisition of a new stationary state. A cell memory influences a change of a baseline component, an amplitude and a frequency of a periodic component, and a maximum expression level and a minimum expression level of an environmental stimulus response component. Among these, a change of a baseline component, and changes of an amplitude and a frequency of a periodic component may be identified independently from a strength of an input from an environment. Paying attention to this point, the local constant region is identified from at least one of a change of a baseline component, a change of an amplitude of a periodic component, and a change of a frequency of a periodic component.

A time series variation of a blood molecule group includes a pattern of a seasonal variation that repeatedly appears on a monthly basis or on a yearly basis in addition to a circadian rhythm of a 24 hour interval. When this is interpreted as a change of a baseline, there is a risk of leading to an erroneous prediction or control scheme. A seasonal component is extracted from a baseline component, and is divided as a periodic component in a long period of time.

In step S8, the identification unit 16 identifies a causal relation. That is, a causal relation between stationary states of respective molecules is created. The dynamic construction model may be used to identify a causal relation.

A constant region of a molecular group in the blood associated with the "cell memory undergoing a time evolution" extracted by this scheme forms a direct or indirect causal relation according to chronological order. To apply the causal relation to a control of progress of a disease, a causal structure is expressed by creating a graph structure associated with a probability structure/causal structure using the constant region as a node.

Figure 3:
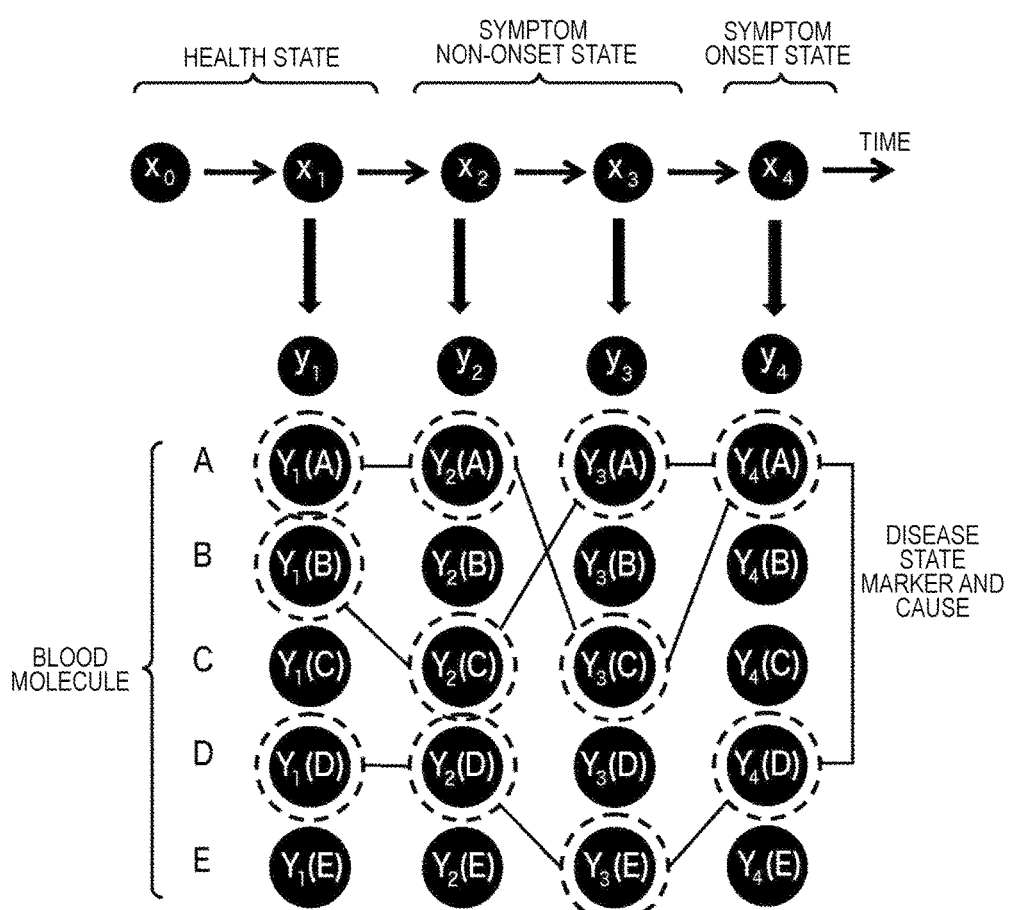
FIG. 3 is a diagram illustrating a model associated with a causal relation using a constant region as a node.

FIG. 3 is a diagram illustrating a model associated with a causal relation using four constant regions $y_1$ through $y_4$ of five blood molecules A, B, C, D, and E as nodes. Referring to FIG. 3, Yi(A) through Yi(E) denote nodes of the constant regions $y_i$ (i=1, 2, 3, and 4) of the blood molecules A through E, respectively, and $x_0$ through $x_4$ denote states of an organism. The states $x_0$ and $x_1$ denote a health state, the states $x_2$ and $x_3$ denote a symptom non-onset state, and the state $x_4$ denotes a symptom onset state. A number indicates a passage of time in a direction from a small value to a large value.

In this model, the node $Y_4(A)$ and the node $Y_4(D)$ are causes, and markers that replace a state of a disease. The node $Y_3(A)$ and the node $Y_3(C)$ affect an induction of the node $Y_4(A)$, and the node $Y_3(E)$ affects an induction of the node $Y_4(D)$. Similarly, the nodes $Y_2(C)$, $Y_2(A)$, and $Y_2(D)$ affect an induction of the nodes $Y_3(A)$, $Y_3(C)$, and $Y_3(E)$, respectively. Further, the nodes $Y_2(A)$, $Y_1(B)$, and $Y_1(D)$ affect an induction of the nodes $Y_2(A)$, $Y_2(C)$, and $Y_2(D)$, respectively.

An inference of the graph structure associated with a causal structure between constant regions of this biological molecule may be formulated as below. First, a value of a stationary state of a biological molecule Molecule 1 is regarded as a random variable. That is, under a circumstance, an amount of Molecule 1 is regarded as an instance of a random variable X1. Observation data processed by the organism local constant model of the embodiment may be regarded as data measuring an instance of a random variable of p types of blood molecules under a circumstance. Since a stationary state is observed in various time periods and circumstances, the observation data processed by the local constant model may be expressed as a data matrix. That is, observation data including n different stationary states is a p×n matrix size. An object of the analysis is to infer a dependency relation in matrix data.

As a scheme of inferring a graph indicating a dependency relation between random variables from a data matrix, various mathematical models such as Boolean network, Bayesian network, a graphical Gaussian model, and an ordinary differential equation are proposed, and may be used for the embodiment. Among these, by assuming a dependency relation expressed using a non-closed path directed graph between random variables, and assuming a Markov chain rule in a dependency relation between a node and a structure of the non-closed path directed graph, an inference using Bayesian network expressed by a product of conditional probabilities based on a given set of random variables with respect to parent variable is useful for the embodiment.

A further detailed adaptation of Bayesian network may apply a scheme used for a data analysis of a DNA chip (333-356, Second issue, Volume 54, Statistical Mathematics, Yoshinori Tamada, Kiyochika Imoto, and Satoru Miyano). Specifically, it is implemented by matching an expression level of a stationary state of the embodiment to an expression level of mRNA of a DNA chip. An existing physiology model may be used as a previous knowledge to infer a stationary state graph structure of the embodiment.

A graph structure is first constructed in an individual level. An existing physiology model may not sufficiently match diversity or diversification of an individual, and thus an error may occur in a graph structure inference. To optimize a graph structure, a plurality of individual graph structures are compared to one another, and classified into a small group having a similar structure, and a graph structure is selected again. In this way, an optimum graph structure is constructed.

A route of a cause and effect leading to a common symptom of a plurality of patients may be different among individuals. As such, an optimum graph structure is determined for each group having the same causal structure rather than causing the optimum graph structure to converge into one.

In step S9, the identification unit 16 identifies a causal relation of molecular markers and a relation with an external environment. That is, a causal relation between respective molecules and a relation with an environment are created. A measurement value of a time series variation of a lifestyle may be used as an external environment.

When an input from an environment may be quantitatively measured, a "constructed change" may be represented and applied to a control by analyzing a mechanism in which stimulus of different intensities received in different periods influences responsiveness of a blood molecule. For example, a negative stress level may be measured by a DRM (Daily Reconstructive Method) (one day constitution method). This divides a day into an average of about 24 degrees for each event, and expresses respective positive and negative values in numerical values of 0 through 6 in a step-by-step manner.

Referring to an influence of meal, by electronically recording content of each meal, it is possible to measure intake information such as calorie, carbohydrate (glucide), fat, protein, vitamin, and phytochemical. In addition, it is possible to measure an amount of intake of a supplement and the like. When a correlation is observed between an environmental stimulus and a change of an expression level of a blood molecule, the environmental stimulus may be used for a control of a change of an expression level of an intended blood molecule, that is, a change in state of an organism.

In step S10, the inference and control unit 17 infers and controls changes in state. That is, a future change in state of an organism of a human is inferred, and an intervention scheme including a prevention scheme is proposed.

An inference of a change in state classifies a group by a mutual similarity of a causal structure between constant regions acquired in step S8. In this way, a future change of a disease preliminary group classified in the same group may be inferred by a causal structure acquired from a patient undergoing a progression of a disease. In addition, a causal structure in which a disease is recovered to a health state without an onset of a disease from a potential change prior to an onset of a disease may be used for a control scheme of preventing an onset of a disease. The causal relation of molecular markers (that is, an internal environment) and a relation with an external environment identified in step S9 may be used for a control.

Second Embodiment

[Application of Dynamic Construction Model to Standardization of Cultured Cell]

Figure 4:
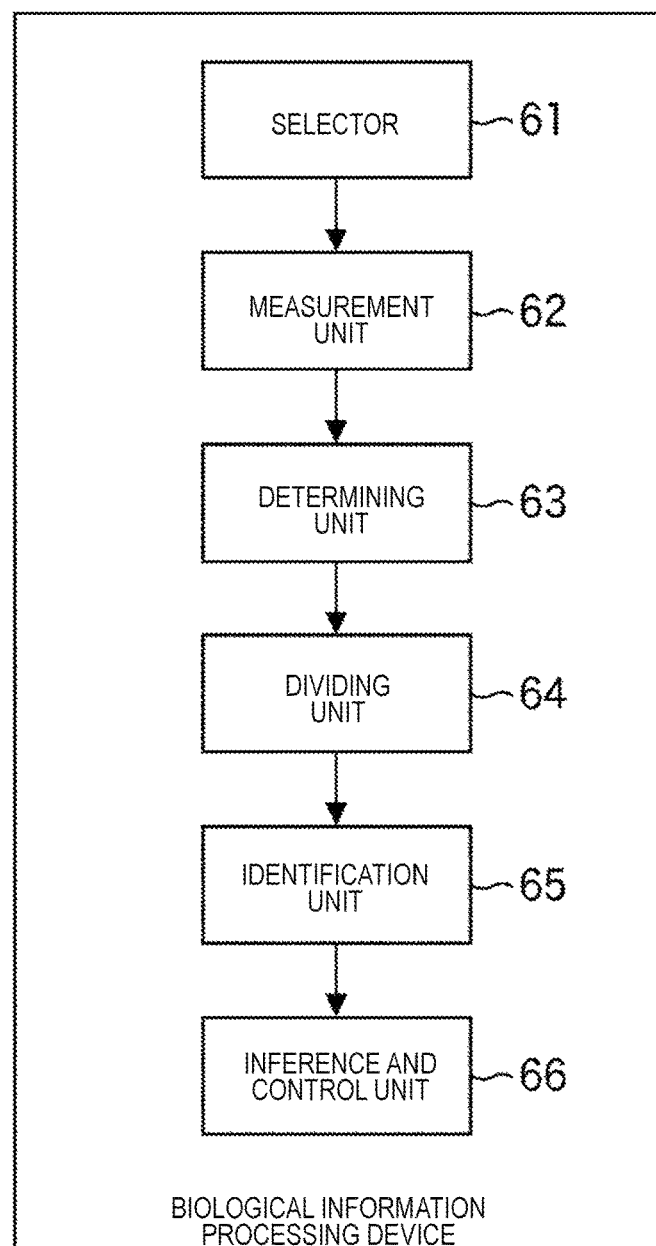
FIG. 4 is a block diagram illustrating a configuration of another embodiment of a biological information processing device.

FIG. 4 is a block diagram illustrating a configuration of a biological information processing device 51 that predicts and controls a cellular state of a cultured cell. The biological information processing device 51 includes a selector 61, a measurement unit 62, a determining unit 63, a dividing unit 64, an identification unit 65, and an inference and control unit 66.

The selector 61 selects measurement molecules. The measurement unit 62 performs a measurement. The determining unit 63 determines a measurement interval. The dividing unit 64 divides components. The identification unit 65 identifies a constant region, and identifies a causal structure between molecular markers and a causal structure of a molecular marker and an environmental condition. The inference and control unit 66 infers and controls a cellular state of a cultured cell.

Figure 5:
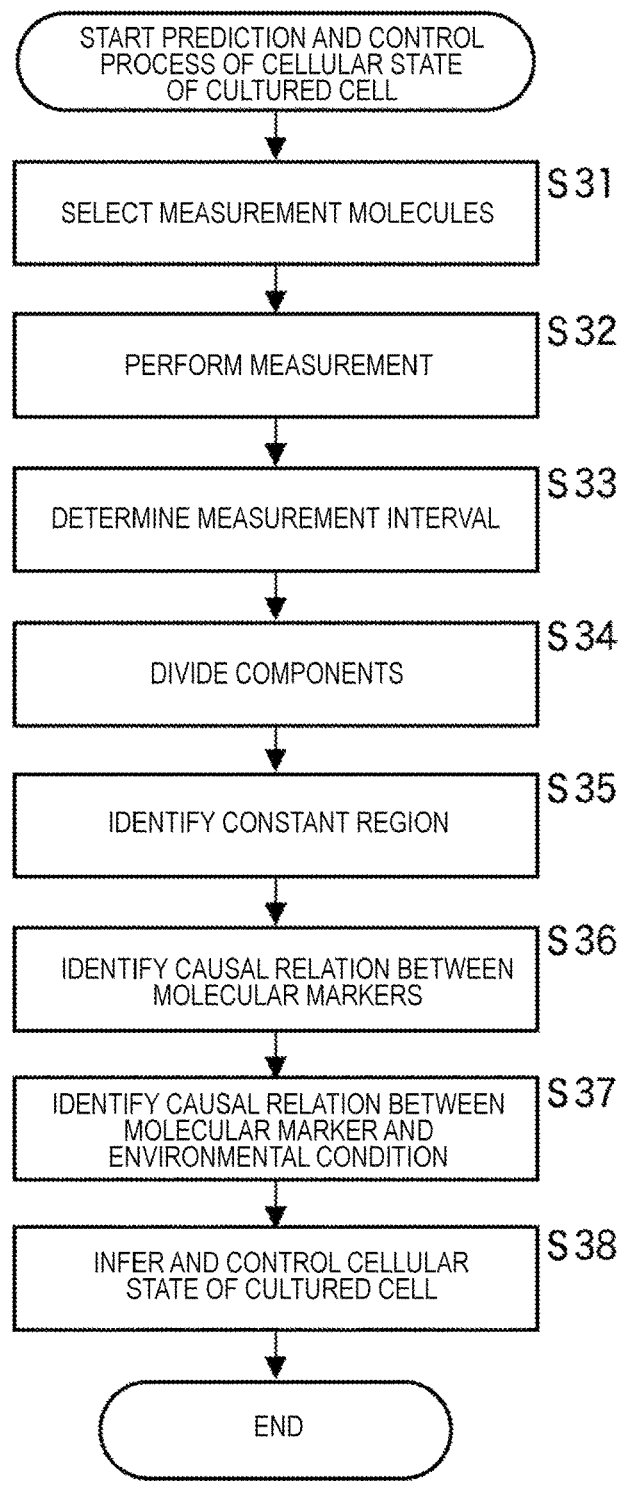
FIG. 5 is a flowchart illustrating a prediction and control process of a cellular state of a cultured cell.

FIG. 5 is a flowchart illustrating a process of predicting and controlling a cellular state of a cultured cell. Hereinafter, a prediction and control process performed by the biological information processing device 51 of FIG. 4 will be described with reference to FIG. 5.

In step S31, the selector 61 selects measurement molecules.

Changing a property involved in cultivation by a cultured cell is a major obstacle in a construction of an evaluation system using a cell or a development of a medicine using a cell as an active ingredient. In a prediction and control of a change in state of a cultured cell, it is possible to perform a formulation with a problem of a state inference of a mesoscale. A state of a mesoscale is expressed by a local extracellular environment formed by a component added in a culture medium and a molecule produced from a cultured cell. As such, in a state prediction and control of a cultured cell, a time series variation of a molecular group produced from a cultured cell and a molecule in a culture medium is measured.

A molecule produced from a cultured cell includes a molecular group expressed in a cell surface in addition to a secretory cell, but excludes an intracellular information transduction molecule or a transcription factor. As a component in a culture medium, it is useful to measure an amount of IGF-I or insulin. As a molecule produced from a cell, an integrin family molecule, a growth factor including FGF-2, EGF, and PDGF in addition to insulin and IGF-I are useful.

In step S32, the measurement unit 62 performs a measurement.

A molecule produced from a cultured cell and a molecule in a culture medium are measured by acquiring a smaller amount of sample when compared to the culture medium. In addition, for a molecule that is acquired by an extracellularly expressed molecule and does not float in a culture medium among molecules produced from a cell, fluorescent labeling is performed on the molecule, and then a quantitative estimation is performed by an image analysis of a cultured cell. In addition, for a molecule that is difficult to be measured, a substitute measurement is performed by a genetic expression of a secretory protein or a membrane protein by using a reporter system within a cell.

In step S33, the determining unit 63 determines a measurement interval.

It is preferable that the measurement interval be in a range of about ten minutes to an hour. When a reporter system is used, continuous data is acquired.

In step S34, the dividing unit 64 divides components. In addition, in step S35, the identification unit 65 identifies a constant region.

To extract information from acquired time-series data of a molecular marker, multivariate time series including a molecule produced from a cultured cell and a molecule in a culture medium is treated in a unified manner as a state space model. The state space model includes two submodels of a system model and an observation model. In general, the two submodels are expressed using a conditional probability as follows.

$$x_n \sim q(x_n | x_{n-1}) \quad (12) \text{ (system model)}$$

$$y_n \sim r(y_n | x_n) \quad (13) \text{ (observation model)}$$

Herein, $y_n$ denotes an observed time series of a multivariable, $x_n$ denotes a k-dimensional vector that may not be directly measured, and q and r denote a conditional distribution of $x_n$ given by $x_{n-1}$ and of $y_n$ given by $x_n$, respectively. In the "biological state space model," $x_n$ expresses a state of an actual cultured cell, and $y_n$ indicates an expression level of a molecule produced from a cultured cell and a molecule in a culture medium that may be measured. When a distribution of an initial state vector $x_0$ is disposed by $p(x_0|0)$, a prediction of a state of a cultured cell may be formulated by an evaluation of $p(x_n|y_n)$, that is, obtaining a distribution of $x_n$ given by an observed value $y_n$ and an initial distribution.

Time-series data $y_n$ of a molecular group produced from a cultured cell may be decomposed into a periodic component using a seasonal adjustment model, an environmental stimulus response component using a multi-linear model, and a baseline component using a polynomial smoothing spline model, respectively, and be extracted. A cell memory of a cultured cell is reflected on an amplitude and a frequency of a periodic component, a maximum expression level of an environmental stimulus response component, and a change of a baseline. Among these, a local constant region associated with an amplitude and a frequency of a periodic component, and a change of a baseline are noted as the "cell memory undergoing a time evolution."

In step S36, the identification unit 65 identifies a causal relation between molecular markers. In step S37, the identification unit 65 identifies a causal structure of a molecular marker and an environmental condition.

A change of an amplitude and a frequency of a periodic component, a change of a baseline, a time change of an artificial component added to a culture medium, and an environmental stimulus response component form direct or indirect causal relation according to a time series. To apply the causal relation to a control of a change in state of a cultured cell, a causal structure is expressed by creating a graph structure associated with a probability structure/causal structure using, as a node, a local constant state of a molecular group in various culture media and a molecular group produced from a cultured cell.

The graph structure is created based on a conventional biological knowledge, and then upgraded to an optimum graph structure using time-series data. A change of a graph structure is solved as a selection problem of a covariance in regression analysis. A route of a cause and effect of a cultured cell leading to the same change in state may be different depending on origins. As such, an optimum graph structure is determined for each group of a cultured cell having the same causal structure rather than causing the optimum graph structure to converge into one. A change in state characteristic of the "biological state space model" is used for a classification of this group. In addition, a causal structure for an intervention by a change of an environmental condition such as a culture medium component, a cell culture density, an oxygen partial pressure, and a temperature is separately created.

In step S38, the inference and control unit 66 infers and controls a cellular state of a cultured cell.

An inference and control of a change in state of a cultured cell may be performed from a causal structure of the past in which a cell originated from the same tissue is cultured in a similar condition. In addition, a control in a direction of obtaining a state of a cell may be performed from a causal structure of a change in state of a cell and a change of an environmental condition such as a culture medium component, a cell culture density, an oxygen partial pressure, and a temperature.

Third Embodiment

Figure 6:
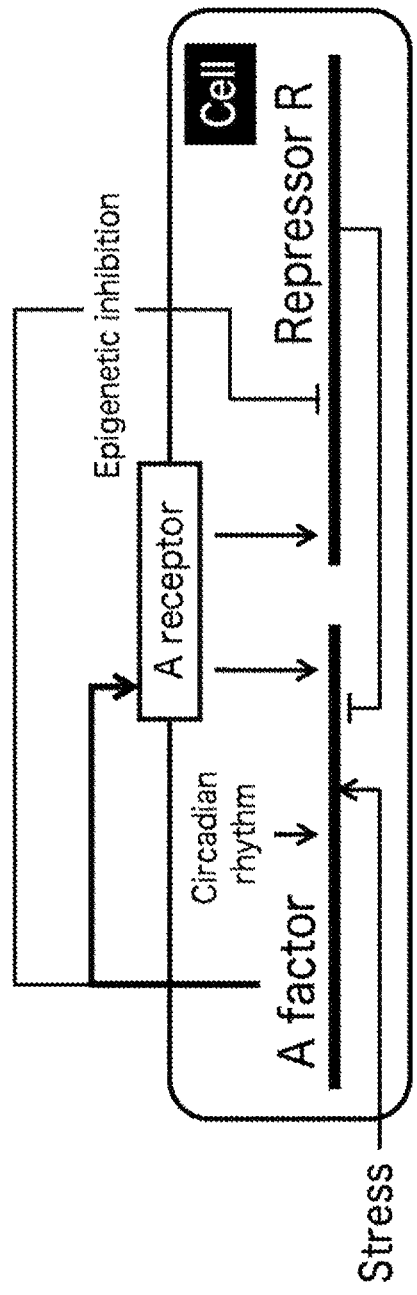
FIG. 6 is a diagram illustrating a configuration of a model of a cell.

Next, a model of a cell that produces a molecule A secreted in the blood is examined. As illustrated in FIG. 6, the cell has the following characteristic.

(1) A control is performed by a circadian rhythm in a stationary state.

(2) An induced expression is generated in response to a stimulus from an environment.

(3) A positive and negative feedback is received by a repressor R and a receptor of the molecule A.

(4) An expression is controlled when the repressor R is epigenetically modified.

Figure 7:
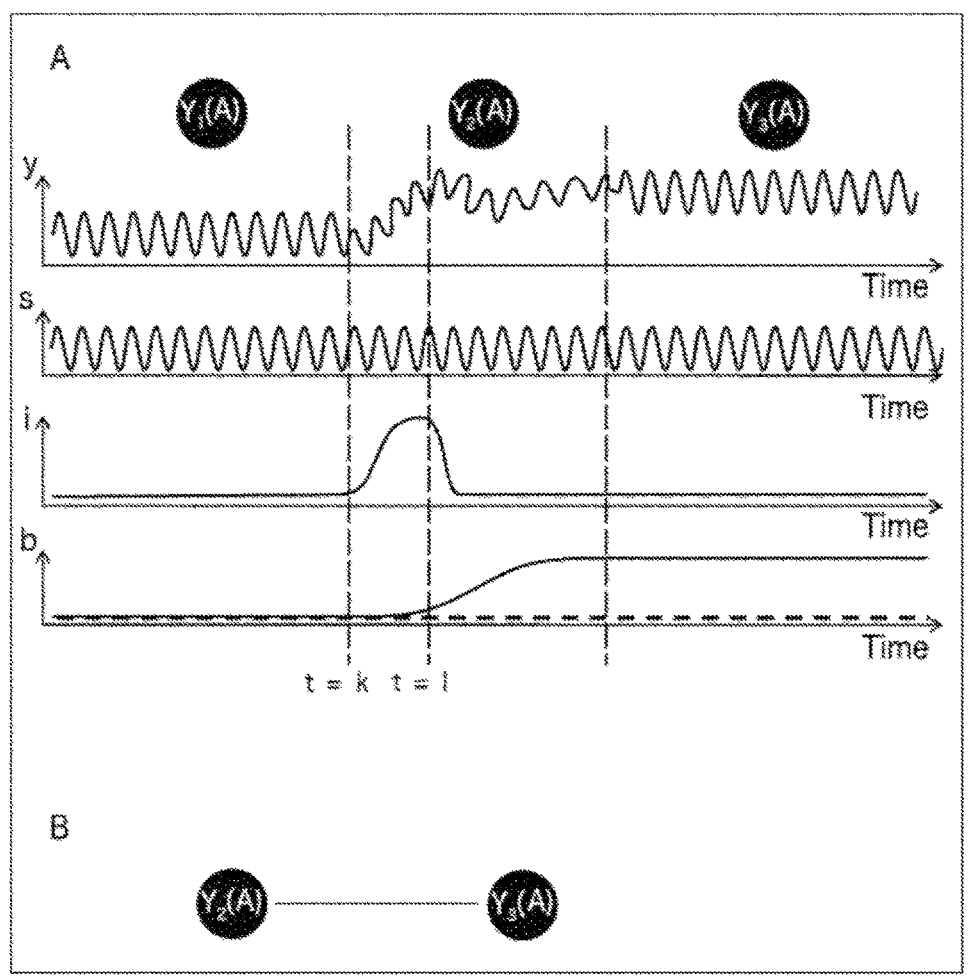
FIG. 7 is a diagram illustrating a change in state of a cell.

A time series variation of the molecule A secreted in the blood from the cell changes as y of A of FIG. 7.

Time-series measurement data y(t) is presumed as follows.

$$y(t)=s(t)+x(t)+b(t)+v(t) \qquad (14)$$

s(t): periodic component
x(t): environmental stimulus response component
b(t): baseline component
v(t): observational error An environmental stimulus response component x(t) is formulated as a multilinear model as follows.

$$x(t)=F(t) \times (t-1)+v(t) \qquad (15)$$

In the above Equation, F(t) indicates a conversion function of an output with respect to an environmental stimulus of a cell, and v(t) indicates an environmental stimulus. Regarding a parameter of the conversion function, an optimum value is searched for using an autoregression model.

A baseline component b(t) is defined as below as a regression model of degree 2, and is used.

$$b(t)=a_{t-1}b(t-1)+a_{t-2}b(t-2)+v_B(t) \qquad (16)$$

Herein, a denotes a regression coefficient, and $v_B(t)$ denotes a noise component. Then, b(t) is expressed as follows.

$$b(t)=H(t,t-1)b(t-1)+V(t,t-1) \qquad (17)$$

Herein, H(t, t−1) is a 2×2 matrix, and V(t, t−1) is two-dimensional noise. An optimized function is selected so that a baseline is smoothed.

A periodic component s(t) is based on a circadian rhythm of a 24 hour interval. Thus, when p observed values are obtained during an interval, the periodic component approximately satisfies the following Equation.

$$s(t)=s(t-p) \qquad (18)$$

When this is expressed using a time delay operator G, the following Equation is approximately satisfied.

$$(1-G^p)s(t)=0 \qquad (19)$$

As such, a periodic component of degree 1 may be formulated as a seasonal adjustment model as below by white noise v(t).

[Equation 3]

$$\left(\sum_{i=0}^{p-1} G^i\right)' s(t) = v(t2) \qquad (20)$$

Using this model, the time-series data of y of A of FIG. 7 is decomposed into a periodic component s, an environmental stimulus response component x, and a baseline component b. Here, i in A of FIG. 7 denotes an induction component.

Next, from a variability characteristic of a baseline, a decomposition is performed into three constant regions of $Y_1(A)$, $Y_2(A)$, and $Y_3(A)$. A cell includes an input from an environment between time k and time 1, and an environmental stimulus response component of $Y_2(A)$ is a direct input with respect to the input. In addition, in this autogenous control model, a time change division $Y_2(A)$ of the molecule A is a cause of changing an expression state of a factor A from $Y_1(A)$ to $Y_3(A)$. As illustrated in B of FIG. 7, this relation is expressed as a change from $Y_2(A)$ to $Y_3(A)$ by a graph structure using, as a node, a constant region associated with an expression level change of the molecule A.

In this way, in each embodiment, it is possible to formulate a time evolutional change of a human organism, to predict and control a change of a biological state that may be used for a health management, a disease prediction, a disease radical cure, and the like.

In addition, it is possible to apply the embodiment to a control of an onset of a chronic disease and a progress of a chronic disease resulting from a long-term lifestyle that may not be treated using a conventional scheme. Further, the embodiment may simultaneously manage commonality and heterogeneity between individuals, and thus is an effective tool for an individual medical care. In addition, the embodiment may control diversification resulting from a time evolution of a cell induced by a cell culture, and be applied to a standardization of a cell evaluation system or a cell therapy.

Fourth Embodiment

Most children born with a low weight as a result of hypogenesis caused by a nutritional insufficiency in the womb grow to catch up the delay by the age of two, thereby having a build of a child born with a standard body weight. When a low caloric diet is received as a diet after the birth, a growth to catch up the delay is inhibited, and a growth may not catch up the delay even with a high caloric diet received after the age of two. When a rapid growth is exhibited to catch up the delay, a risk of observing an insulin resistance in the future increases (Rotteveel, J. et al. European Journal of Endocrinology 158; 899-904, 2008). Even when a build is recovered, a decrease in a differentiation efficiency of a pancreatic β cell changed by epigenetics to adapt to a nutritional environment in the womb, responsiveness of an insulin signal, an appetite level, a stress responsiveness, and the like are not recovered, which is inferred as a cause.

However, not all low-weight babies, resulting from hypogenesis, exhibiting a growth to catch up the delay undergo an onset of an insulin resistance. An insulin secretory ability, an insulin signal responsiveness, an appetite level, and a stress responsiveness of each individual do not exhibit a rapid change such as a growth to catch up the delay, while being changed by a lifestyle. Thus, by monitoring an amount of insulin in the blood, an amount of leptin in the blood, an amount of glucocorticoid in the blood, a blood-sugar level, an caloric intake, and the like using a scheme of the embodiment, it is possible to predict and control an obesity trend, an insulin resistance onset trend, and the like.

Specifically, when a relation of caloric intake by eating, an amount of insulin secretion after eating, and a time change of a blood-sugar level is measured and compared each day, it is possible to measure that an amount of production per caloric intake of an insulin secretion, and a change of a strength of insulin responsiveness change from a stationary state to another stationary state. A change of a stationary state may be classified into a change in a direction in which an insulin resistance is improved and a change in a direction in which an insulin resistance is degraded. An increase in an amount of insulin secretion and a strength of insulin responsiveness is a change in an improving direction, and the opposite is a change in a degrading direction.

Using a scheme of the embodiment, an amount of secretion of glucocorticoid or leptin may be first formulated as a change from a stationary state to another stationary state. When an amount of production of leptin with respect to a predetermined caloric intake is low, a suppression of food intake is reduced, and an obesity trend is increased. When an amount of glucocorticoid is high, an obesity trend and a circulatory system disease onset trend are increased through a plurality of active sites. Thus, a change of a stationary state in a direction in which an amount of secretion of glucocorticoid is decreased and an amount of secretion of leptin is increased is a change in a direction in which an insulin resistance and an onset trend of an associated disease are improved.

One of characteristics of the embodiment is widely tracking a time change of a molecule within various organisms. Thus, the embodiment may use an insulin secretion, insulin responsiveness, a glucocorticoid secretion, and a leptin secretion to identify an unknown molecule within an organism involved in a change from a stationary state to another stationary state. In addition, by clarifying a relation of a new associated biological molecule and a record of a lifestyle using a scheme of the embodiment, it is possible to propose a new improvement scheme for improving an insulin resistance or obesity.

Fifth Embodiment

An amount of DHEA-S in the blood in which sulfuric acid is added to dehydroepiandrosterone starts to increase at the age of about six to seven, reaches a peak at the age of about twelve to thirteen, maintains the high value until the age of about thirteen to twenty-five, and then linearly decreases with aging, for both sexes. In a long-term follow-up research, a plurality of researches all parts of the world clarify that a DHEA-S value in the blood of a male is inversely correlated with a death rate or an onset of a cardiovascular disease (vol 5. No 1. 42-46, 2009, antiaging medicine, Toshihiko Yanase). However, currently, it is unclear what decreases an amount of production of DHEA-S. According to the embodiment, a biological molecule associated with changing an amount of DHEA-S secretion from a stationary state to another stationary state, and a lifestyle associated with a change of the biological molecule may be clarified, a new proposal of a scheme of inhibiting a decrease in DHEA-S may be performed.

Sixth Embodiment

A most effective scheme for delaying aging and increasing a life expectancy is a restriction of calories. A restriction of calories is a restriction of calories performed while taking optimum nutrition rather than merely reducing a size of a meal. However, sufficient scientific evidence regarding optimum nutrition or an appropriate caloric restriction level is not present. The embodiment may be used to clarify an optimum nutrition intake level or caloric intake level at an individual level.

For example, when a restriction of calories is imposed on a patient who is likely to get diabetic, it is possible to measure a time series variation of c-reactive protein (CRP) corresponding to an inflammatory index, and an adiponectin production and an active oxygen production corresponding to an index of a qualitative change of a fat cell. In this way, it may be formulated that a state of a fat cell, an active oxygen stress state, and an inflammatory state change from a stationary state to another stationary state.

In addition, the embodiment may also be used to identify a new biological molecule associated with a change from the stationary state to another stationary state. A newly discovered time-series record associated with a biological molecule marker and a meal may be used to individually optimize a nutritional intake and a caloric intake.

Seventh Embodiment

A difference in sensitivity to stress induces an onset of depression or suicide entailed by chronic stress. Sensitivity to stress depends on a strength of a negative feedback of a neuron of glucocorticoid responsiveness projected from a hippocampus to an amygdaloid nucleus. In addition, a strength of a negative feedback of the neuron depends on epigenetic modification of a glucocorticoid receptor gene. When a suicide is compared with a control group as to epigenetic modification of the neuron, it is indicated that a person suffering from child abuse or child neglect has a glucocorticoid receptor gene suppressed by epigenetic modification (Hyman, S. Nature Neuroscience Vol. 12, No. 3, 241 243, 2009).

When a level of sensitivity to stress is identified, it is possible to prevent an onset of depression by quantitatively identifying a person who is likely to undergo an onset of depression, and providing an appropriate environment. When a time series variation of glucocorticoid in the blood is measured at short intervals of about ten minutes using the embodiment, the time series variation may be divided into a daily variation component and a stimulus dependent component. Using the daily variation component, an average amount of secretion of glucocorticoid in the blood at a measurement date may be calculated. In addition, using the stimulus dependent component, a relative strength of a negative feedback may be calculated by measuring a maximum amount of secretion and duration. Accordingly, when the embodiment is applied, it is possible to measure sensitivity to stress, and to track a process in which sensitivity to stress changes with a lifestyle.

The most notable hypothesis associated with a depression onset mechanism regards, as a cause, a lowering of BDNF (Brain Derived Neurotrophic Factor) which is a neurotrophic factor (Shi, Y. et al. Psychiatry and Clinical Neuroscience 64, 249-254, 2010). BDNF is produced from pro-BDNF (BDNF precursor) by t-PA (tissue-type plasminogen activator). That is, using the embodiment, it is possible to infer an onset or a curative effect of depression by observing a time series variation of BDNF, pro-BDNF, and t-PA in the blood, and identifying a change from a stationary state to another stationary state. In addition, the embodiment may be used to discover a new biological molecule marker associated with an onset and prevention of depression.

Eighth Embodiment

A chronic overwork such as a nursing care of a partner and psychological stress increases a frequency of an infectious disease, reduces the ability of wound healing, and increases a frequency of high pressure or a liver illness. A biomarker associated with the chronic overwork and psychological stress includes inflammatory cytokine IL-6 (interleukin 6). It is known that IL-6 is associated with a circulatory system disease, an osteoporosis, type 2 diabetes, cancer, a gum disease, fragile habitus, organ failure, and the like that develop aging dependently. IL-6 is induced to develop through experience entailing depression, negative feelings, and stress. In addition, an increase in IL-6 in the blood with is noticeable in people engaged in nursing care when compared to people not engaged in nursing care (Kiecolt-Glaser J K et al. Proc. Natl. Acad. Sci. USA 100: 9090-9095). As such, by tracking a change in expression level of IL-6, it is possible to predict and prevent an onset of an age-related disease or a stress-related disease.

Ninth Embodiment

A human body is an open system, and a future of a body condition is not a mere repetition of the past. A cell memory of the technology may acquire a process in which an organism undergoes a time evolution according to a history only by a measurement of a biological molecule, and formulate the process. To apply this formulated time-based change to an individuated health care, appropriate options of a future lifestyle need to be provided based on diversity and diversification of an individual.

In addition, DNA-sequence information of individuals inherited from parents is useful for inference of substance of diversity and diversification of the past before initiating a biological state measurement of individuals based on the technology. A current diversity of each individual is formed by hereditary diversification and a lifestyle of the past. As such, by integrating three pieces of environmental information based on cell memory information, DNA polymorphism information, and a lifestyle of a biological molecule undergoing a time evolution of the technology, it is possible to enhance accuracy of a future prediction of health.

With development of base arrangement technology, it is possible to analyze a full-genome sequence of individuals. From a sequencing analysis, it is possible to detect a single nucleotide polymorphism and structural polymorphism included in individuals. A relation between a genetic diversity and health or illness may be classified into four types of a chromosome anomaly, a monogenic disease, a multifactorial genetic disease, and an idiopathic disease (Thompson & Thompson "Genetic Medicine, Seventh Edition" Medical Science International, 2009).

A human somatic cell contains 23 pairs, 46 chromosomes, and 22 pairs among them are autosomal chromosomes excluding a difference between the sexes. A remaining pair is referred to as a sex chromosome. A female has two X chromosomes, and a male has an X chromosome and a Y chromosome. An onset frequency of a chromosomal abnormality is high, and about six new born babies per every 1,000 new born babies are affected. Among chromosomal abnormalities, an abnormality corresponding to an increased number of chromosomes frequently occurs. When the number of chromosomes increases by one, it is referred to as trisomy. For example, trisomy 21 causes a disease called Down syndrome. About one of every 800 people is born with Down syndrome.

A frequency at which a baby is born with Down syndrome exponentially increases with an age of a mother, and about 1% of babies are born with Down syndrome when the age is 45 or more. A main issue of Down syndrome is a mental retardation. However, furthermore, a risk of leukemia increases, and a lot of patients with Down syndrome develop dementia of the Alzheimer type after the age of 40. 90% of causes of trisomy 21 are included in a process of a reduction division that forms an egg of a mother. As such, a trisomy 21 abnormality occurs from a moment of the fertilization. However, a symptom occurs in various periods, and a "time delay" is included between a formation of a hereditary cause and an onset of illness.

A monogenic disease is a disease that develops as a result of genomic mutation of a gene, and is referred to as a Mendelian disorder. So far, 3917 types of Mendelian disorders are being reported. A mode of inheritance includes a dominant mode and a recessive mode. A dominant mode is a mode of inheritance that develops only by inheriting a genetic mutation from one of a mother and a father. A partially recessive mode indicates a mode of inheritance that develops only when a genetic mutation is inherited from both parents. It is known that a monogenic disease is realized by 2% of a group at a time of life.

A monogenic disease is a disease that mostly develops during childhood. However, about less than 10% of monogenic diseases experience symptoms after puberty. Further, 1% or less may experience symptoms later in life after the end of the reproductive years. Regardless of a period in life in which a symptom starts, a "time delay" is observed between an acquisition of variation and an onset of symptoms.

A disease observed at birth such as a congenital anomaly, and a chronic disease that develops at a middle age such as cardiac infarction, cancer, diabetes, rheumatism, a mental disease, dementia, and the like are referred to as a multifactorial disorder. A frequency at which this type of disease appears at birth is about 50 people per every 1,000 people. However, since a lot of people are affected by a chronic disease, it is about 600 people per every 1,000 people when seen from a group. A plurality of genetic factors combines for an onset, in which a regular exposure or a chance exposure to a particular environmental factor is considered to be involved. A genetic influence of this multifactorial disorder is analyzed by a scheme referred to as a genome-wide association study (GWAS).

An idiopathic disease is positioned between a mendelian genetic variation and a multifactorial disorder. Parkinson's disease or Alzheimer's disease is included in an idiopathic disease in addition to a familial disease. Unlike a multifactorial disorder, an individual genome sequence analysis needs to be used to identify this sporadic variation.

For any of a chromosome anomaly, a mendelian monogenic disease, a multifactorial disease, and an idiopathic disease, a time delay is included between an acquisition of variation and an onset. In addition, it is inappropriate to describe that a plurality of environmental factors causes a disease to develop as an instant responsive reaction. A "time delay" is included between a point in time when a hereditary factor and an environmental factor are included and a point in time when a disease develops. That is, a hereditary factor and an environmental factor create a potential change in an organism as a cell memory, which is actualized as a symptom when the hereditary factor and the environmental factor form a combination.

A cell memory is acquired when a change of an environmental condition is added to genetic polymorphism, and thus quantitatively recording an environmental condition is effective for a future prediction of health. Among environmental conditions, an exterior environment such as stress, a diet habit, an exercise habit, an infection history, and a cure history may be quantitatively measured.

Stress is recognized when individuals do not adapt to the environment, and feeling stress is different between people for the same environmental condition. Thus, stress may not be identified only from an environmental condition. It is effective to record stress by, for example, a Daily Reconstruction Method (DRM scheme) (Kahneman D, Krueger A B, Schkade D A, Schwarz N, Stone A A. "A survey method for characterizing daily life experience: the day reconstruction method." Science. 306: 1776-1780, 2004).

This scheme divides an event of a day into 24 degrees, and records respective mental positive and negative values. In this way, it is possible to identify a stress coping circumstance at each moment. By continuing the recording, stress may be classified into a short term stress of about several hours to a day, a medium-term stress of about several days to a month, and a long term stress of over several months.

With regard to a diet habit, by recording content of meals divided into cooking ingredients, it is possible to record an amount of intake of calorie, a carbohydrate ratio, a protein ratio, a type and amount of fat, vitamin, phytochemical, trace metal (iron, zinc, copper, cobalt, iodine, selenium, manganese, molybdenum, chrome, boron, and vanadium), drinking (alcohol), and the like.

With regard to an amount of exercise, it is possible to automatically measure a quality or quantity of walking and running using a portable device including an acceleration sensor.

An infection history or a cure/dosing history may be identified by electronic chart data of a private medical doctor. In addition, a Chinese medicine or a general medicine taken by an individual may be recorded by the individual.

As described in the foregoing, a genetic diversity of individuals may be classified using a single nucleotide polymorphism and a structural polymorphism of DNA which is a cause of a chromosome anomaly, a monogenic disease, a multifactorial genetic disease, and an idiopathic disease. It is possible to quantitatively record a time-based change of an environmental condition using a stress state, an intake ingredient taken by a meal, an amount of exercise, an infection history, a cure/dosing history.

To integrate three pieces of environmental information based on cell memory information, DNA polymorphism information, and a lifestyle of a biological molecule undergoing a time evolution of the technology, a relation among three small groups below is clarified using a conditional probability. The three small groups are a small group divided based on a genetic diversity, a small group divided based on a change of an environmental condition, and a small group divided based on cell memory information of a biological molecule. The small group divided based on a genetic diversity is a group based on a genetic diversity of a single nucleotide polymorphism and a structural polymorphism of DNA which is a cause of a chromosome anomaly, a monogenic disease, a multifactorial genetic disease, and an idiopathic disease.

The small group divided based on a change of an environmental condition is a group based on an environmental condition such as a stress state, a diet habit, an exercise habit, an infection history, a cure/dosing history. The small group divided based on cell memory information of a biological molecule is a group based on a change of a biological state represented by FIG. 3 produced from a process illustrated in the flowchart of FIG. 2.

Figure 8:
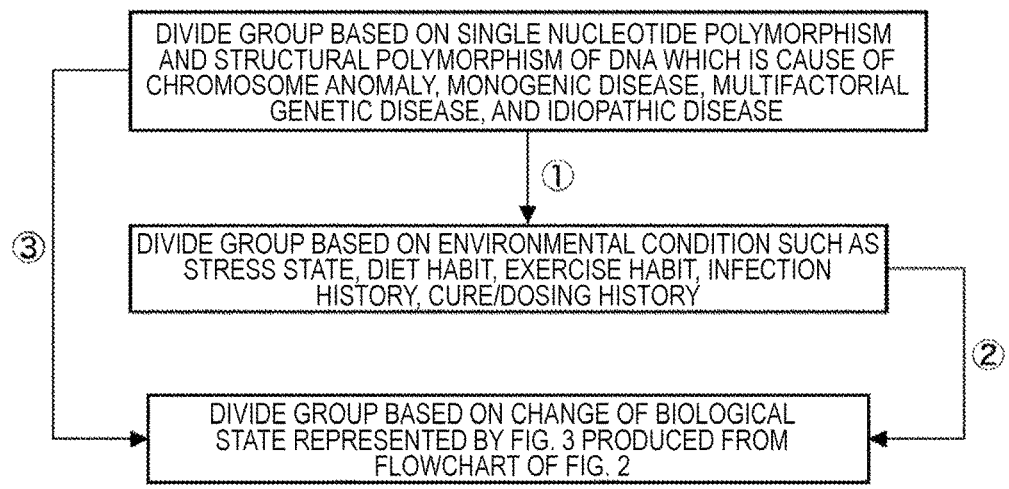
FIG. 8 is a diagram illustrating a causal relation of information.

As illustrated in FIG. 8, the relation of a conditional probability of a group may be broadly classified into the following three relations.

i) Relation between a genetic diversity and an environmental condition ii) Relation between an environmental condition and a biological state iii) Relation between a genetic diversity and a biological state Applying the technology to an individuated health care is providing options of the future to maintain health based on data of a cell memory of the past of a subject of a health care indicated as a causal relation between constant regions of an expression level of a molecule of an organism. A scheme of identifying options of the future include referring to a record of a lifestyle of another person (that is, a person other than a subject) synthetically having a history similar to that of the subject such as a history of gene information, a history of an environmental condition, and a history of a biological state. This scheme may be implemented by clarifying a similarity in a correlation among cell memory information of a biological molecule of individuals, gene information such as DNA polymorphism information, and environmental information based on a lifestyle illustrated in FIG. 8.

The similarity of data may be determined by applying a conventional clustering method. The clustering method may be broadly classified into a division type clustering and a hierarchal clustering. Specifically, it is possible to apply a scheme described in A. K. Jain, M. N. Murthy and P. J. Flynn, Data Clustering: A Review, ACM Computing Reviews, (1999) or Ying Zhao and George Karypis, "Hierarchical Clustering Algorithms for Document Datasets", Data Min. Knowl. Discov. 10(2): pp. 141-168 (2005).

Figure 9:
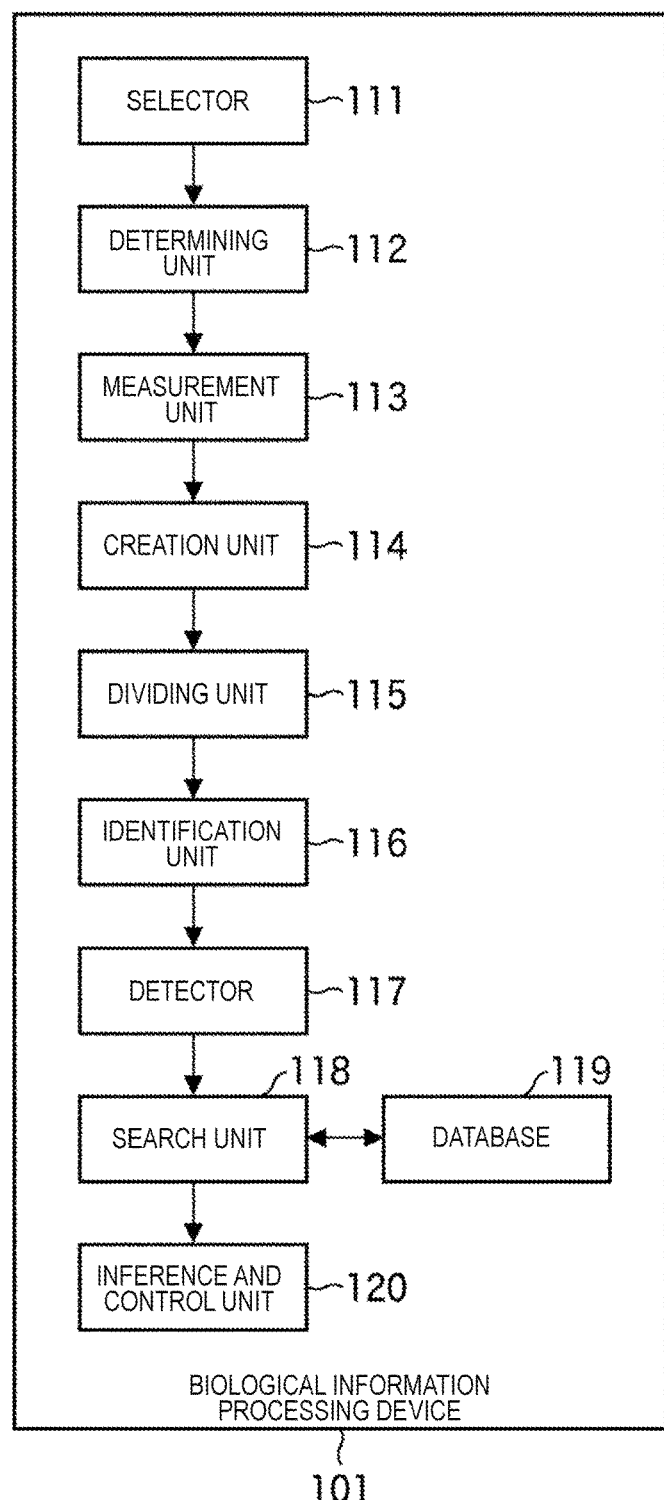
FIG. 9 is a block diagram illustrating a configuration of another embodiment of a biological information processing device.

When a process of the embodiment is performed, a biological information processing device 101 is configured as illustrated in FIG. 9. The biological information processing device 101 includes a selector 111, a determining unit 112, a measurement unit 113, a creation unit 114, a dividing unit 115, an identification unit 116, a detector 117, a search unit 118, a database 119, and an inference and control unit 120. Functions of the selector 111, the determining unit 112, the measurement unit 113, the creation unit 114, the dividing unit 115, the identification unit 116, and the inference and control unit 120 are basically similar to functions of the selector 11, the determining unit 12, the measurement unit 13, the creation unit 14, the dividing unit 15, the identification unit 16, and the inference and control unit 17 illustrated in FIG. 1. As such, description may be repeated, and thus will be provided.

The detector 117 detects gene information. The search unit 118 searches for a similar history from the database 119.

The database 119 stores information of multiple individuals by classifying the information into any one of the three small groups described above with reference to FIG. 8. That is, information of examination results of multiple people obtained by performing the process of FIG. 2 described in the foregoing is stored. In addition, in this instance, a measurement/examination for obtaining information used to determine one of the three small groups to be classified into is added. Specifically, a measurement/examination that specifies a genetic diversity of a single nucleotide polymorphism and a structural polymorphism of DNA is added in addition to a measurement/examination of an environmental condition such as a stress state, a diet habit, an exercise habit, an infection history, a cure/dosing history, and a measurement/examination of cell memory information of a biological molecule.

Figure 10:
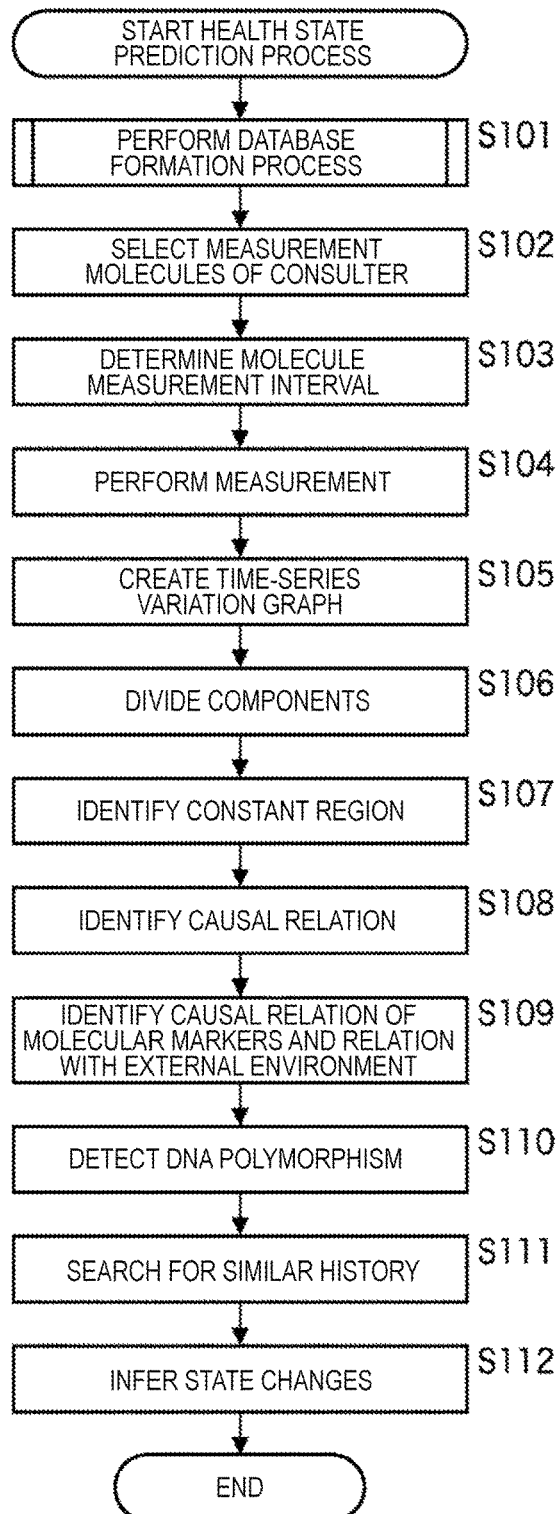
FIG. 10 is a flowchart illustrating another health state prediction and control process.

This process of the embodiment is illustrated in a flowchart of FIG. 10. Hereinafter, the process of the embodiment will be described with reference to FIG. 10.

In step S101, a database formation process is performed. That is, the process illustrated in the flowchart of FIG. 2 is performed on multiple individuals concurrently with a measurement/examination that specifies a genetic diversity of a single nucleotide polymorphism and a structural polymorphism of DNA of each individual, and a result is stored in the database 119. However, information is stored in a form of concealing privacy of individuals.

As described in the foregoing, the information stored in the database 119 is classified into a group based on a genetic diversity, a group based on a change of an environmental condition, and a group based on cell memory information of a biological molecule. Then, three relations below of each group are analyzed using a conditional probability.

i) Relation between a genetic diversity and an environmental condition ii) Relation between an environmental condition and a biological state iii) Relation between a genetic diversity and a biological state For convenience of description, the database formation process is described as step 1 of a health state prediction process of the flowchart of FIG. 10. However, when a database is previously generated using a scheme and is present, the database may be used. In this case, the database formation process may be skipped.

Processes of step S102 through S109 of FIG. 10 are basically similar to step S1 through step S8 of FIG. 2. Description will be briefly made since it is repeated. That is, in step S102, the selector 111 selects measurement molecules of a subject of a health care. In step S103, the determining unit 112 determines a molecule measurement interval. In step S104, the measurement unit 113 measures the measurement molecules, selected in a process of step S102, at the molecule measurement interval determined in step S103.

In step S105, the creation unit 114 creates a time-series variation graph. That is, a graph is created based on Equation (5) through (11) described above. In addition, in step S106, the dividing unit 115 divides components. That is, using a biological state space model, time-series data is divided into a periodic component, an environmental stimulus response component, and a baseline component.

In step S107, the identification unit 116 identifies a constant region. That is, a constant region is identified using an "organism local constant model." In step S108, the identification unit 16 identifies a causal relation. That is, a causal relation between constant regions of each molecule is created. A dynamic construction model may be used to identify the causal relation.

In step S109, the identification unit 116 identifies a causal relation of molecular markers and a relation with an external environment. That is, a causal relation between respective molecules, and a relation with an environment are created. A measurement value of a time series variation of a lifestyle may be used as an external environment. Measurement values are input by the subject, or are input by a measurement device, and the like.

Through the processes above, environmental information and cell memory information of an organism of the subject are obtained.

In step S110, the detector 117 detects DNA polymorphism. That is, the detector 117 detects a single nucleotide polymorphism and a structural polymorphism as gene information of a gene included in the subject of a health care.

When a history of the subject is obtained as described in the foregoing, the search unit 118 searches for a history of another person similar to the history of the subject from information stored in the database 119 in step S111. That is, as described in the foregoing, a similarity in a correlation among cell memory information of a biological molecule of individuals, gene information such as DNA polymorphism information, and environmental information based on a lifestyle is determined, and a most similar history is searched for.

Figure 11:
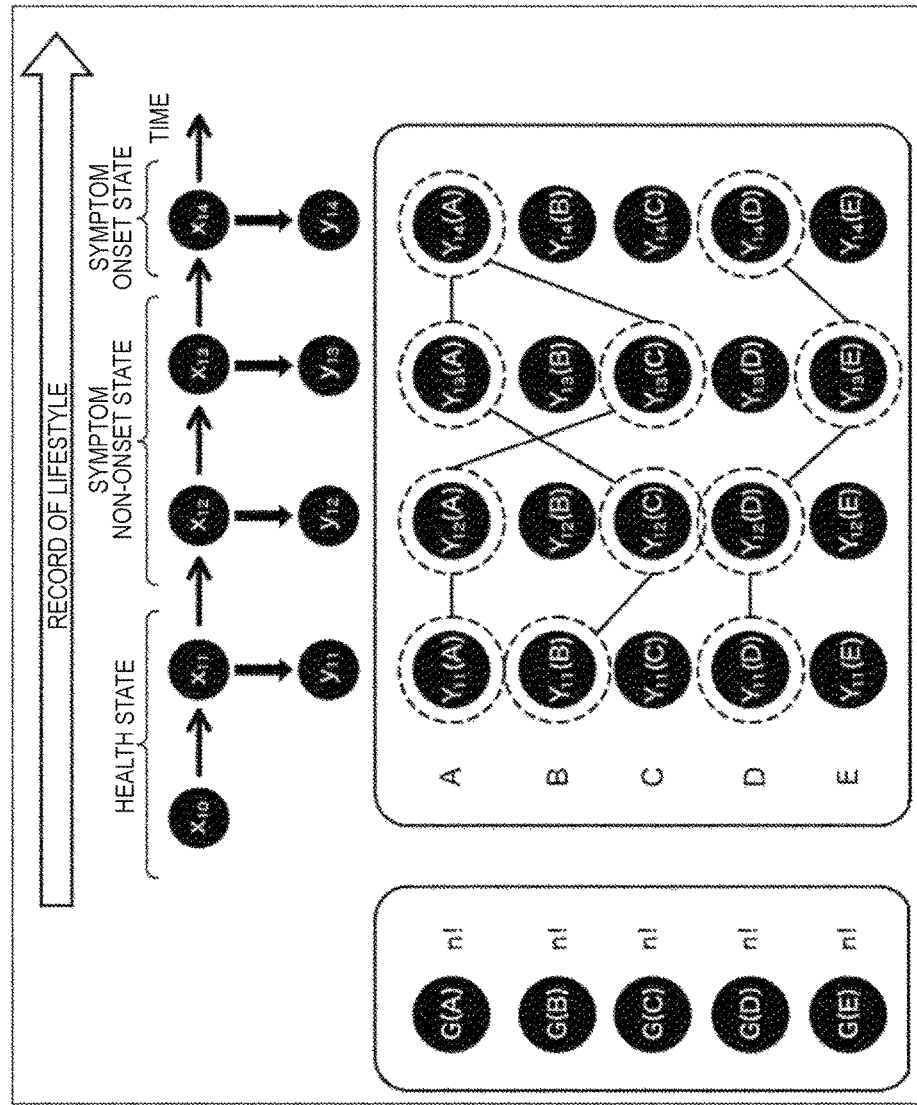
FIG. 11 is a diagram illustrating a model associated with a causal relation of a lifestyle.

A search for a similar history will be described with reference to FIGS. 11 and 12. For example, as illustrated in FIG. 11, it is presumed that five blood molecules A through E of a subject of a health are selected depending on an intention, and are measured. Similarly to a case in FIG. 3, FIG. 11 is a diagram illustrating a model associated with a causal relation using four constant regions $y_{11}$ through $y_{14}$ of the five blood molecules A, B, C, D, and E as nodes. Yi(A) through Yi(E) denote nodes of the constant regions $y_i$ (i=11, 12, 13, and 14) of the blood molecules A through E, respectively, and $x_{10}$ through $x_{14}$ denote states of an organism. The states $x_{10}$ and $x_{11}$ denote a health state, the states $x_{12}$ and $x_{13}$ denote a symptom non-onset state, and the state $x_{14}$ denotes a symptom onset state. A number indicates a passage of time in a direction from a small value to a large value, and a lifestyle of the subject is recorded in the order.

The node $Y_{14}(A)$ and the node $Y_{14}(D)$ are causes, and markers that replace a state of a disease. The node $Y_{13}(A)$ and the node $Y_{13}(C)$ affect an induction of the node $Y_{14}(A)$, and the node $Y_{13}(E)$ affects an induction of the node $Y_{14}(D)$. Similarly, the nodes $Y_{12}(C)$, $Y_{12}(A)$, and $Y_{12}(D)$ affect an induction of the nodes $Y_{13}(A)$, $Y_{13}(C)$, and $Y_{13}(E)$, respectively. Further, the nodes $Y_{11}(A)$, $Y_{11}(B)$, and $Y_{11}(D)$ affect an induction of the nodes $Y_{12}(A)$, $Y_{12}(C)$, and $Y_{12}(D)$, respectively.

Figure 12:
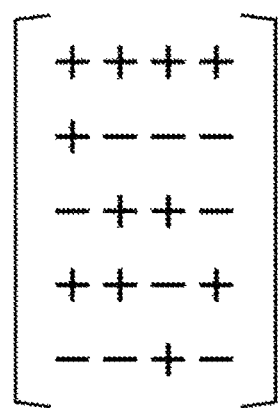
FIG. 12 is a diagram illustrating a matrix representing a history of a cell memory.

When a case in which a cell memory is introduced is denoted by a sign +, and a case in which a cell memory is not introduced in denoted by a sign − in each constant region, a history of a cell memory of a subject in FIG. 11 may be expressed as a matrix of FIG. 12. The sign + and the sign − of FIG. 12 correspond to states of the nodes $Y_{11}(A)$ through $Y_{14}(E)$ of FIG. 11, respectively.

Further, it is presumed that five types of associated molecules G(A) through G(E) are detected as gene information of a gene associated with the blood molecules A through E. When n types of diversities in each gene are included in a compared group from a result of a genome analysis, the group may be classified into n!×5 (! denotes factorial) small groups (group illustrated in the left frame in FIG. 11) from genome information.

When a search for a similar history is executed, data is first classified into small groups according to genome information, and then approximate data is selected from a homogeny of the matrix illustrated in FIG. 12. When a homogeny is the highest, all items of the matrix match one another. When it is partially approximate, proximity is ranked according to a size. Since a record of a lifestyle is attached to data of a matrix, a subject may select a future lifestyle with reference to similar lifestyle information of another person.

In step S112, the inference and control unit 120 infers and controls a state change. That is, a future change in a state of an organism of a subject is inferred, and an intervention scheme including a prevention scheme is proposed.

A simplest proposal is to present a search result of step S111 to a subject. That is, in a search process of step S111, a history of another person similar to a history of a subject is searched for. When the other searched person has a disease or an illness, the subject is highly likely to have a similar disease or illness. Thus, for example, the subject may prevent the similar disease or illness by changing a lifestyle so that an environmental condition is different from that of the other person.

Furthermore, further options for maintaining health of the subject may be actively constructed and provided. For example, among environmental conditions such as stress, a diet habit, an exercise habit, an infection history, and a cure history, it may be suggested that an element having a strong causal relation is specified, and the element is changed. Further, when a factor associated with a gene may be changed, the change may be suggested.

As described in the foregoing, by searching for information of an organism of a person other than a subject similar to cell memory information, environmental information, and gene information of the subject of a health case, it is possible to reliably obtain appropriate information for maintaining health of the subject.

In this specification, a step describing a process of a flowchart includes a process executed in parallel or individually even though the process is not a time series process in addition to a process executed in a time series manner according to an order.

In addition, embodiments of the technology are not limited to the embodiments described above, and may be variously changed within a scope not departing from the spirit of the technology. For example, two or more arbitrary embodiments may be combined together.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

REFERENCE SIGNS LIST

1 Biological information processing device
11 Selector
12 Determining unit
13 Measurement unit
14 Creation unit
15 Dividing unit
16 Identification unit
17 Inference and control unit
51 Biological information processing device
61 Selector
62 Measurement unit
63 Determining unit
64 Dividing unit
65 Identification unit
66 Inference and control unit

The invention claimed is:

1. A biological information processing method comprising the steps of:
measuring an extracellular expression level of biological molecules in an organism over a predetermined time interval;
creating time-series data y(t) showing changes in the measured extracellular expression level over the predetermined time interval;
creating baseline data b(t) by extracting from the time-series data y(t) at least one of a periodic component of the measured extracellular expression level of the time series data y(t) and an environmental stimulus response component of the measured extracellular expression level of the time series data y(t);
dividing the baseline data b(t) into a plurality of constant regions based on changes in magnitude of the baseline data over the predetermined time interval;
creating a matrix of data having a p×n matrix size, where n represents the constant regions for p types of biological molecules;
predicting onset of a disease based on a pattern of change across nodes of the matrix, the pattern determined from measured expression levels of biological molecules known to have the disease; and
treating for the predicted disease,
wherein the time-series data y(t) is expressed by the following Equation 1:

$$y(t)=s(t)+x(t)+b(t)+v(t) \qquad \text{Equation 1,}$$

where s(t) is the periodic component, x(t) is the environmental stimulus response component, b(t) is the baseline data, and v(t) is an observational error.

2. The biological information processing method according to claim 1, wherein the environmental stimulus response component includes one or more change in magnitude of the measured extracellular expression level of the time series data y(t) caused by an external environment.

3. The biological information processing method according to claim 1, wherein the measuring step comprises measuring a glucose level.

4. The biological information processing method according to claim 1, wherein the molecules are blood molecules of the organism.

5. The biological information processing method according to claim 1, wherein the molecules are molecules associated with metabolic syndrome.

6. The biological information processing method according to claim 1, wherein the molecules are molecules in a culture medium.

7. The biological information processing method according to claim 1, wherein the environmental stimulus response component is formulated using the following multilinear model expressed by Equation 2:

$$x(t)=F(t)\times x(t-1)+v_x(t) \qquad \text{Equation 2,}$$

where x(t) is the environmental stimulus response component, F(t) represents a conversion function of an output with respect to an environmental stimulus, and $v_x(t)$ represents a change of an environmental stimulus.

8. The biological information processing method according to claim 1, wherein the baseline data is expressed by the following Equation 3:

$$b(t)=H(t,t-1)b(t-1)+V(t,t-1) \qquad \text{Equation 3,}$$

where b(t) is the baseline data, H(t, t−1) is an m×m matrix, and V(t, t−1) is a matrix associated with m-dimensional noise.

9. The biological information processing method according to claim 1, wherein the periodic component is formulated as a seasonal adjustment model as expressed in the following Equation 4:

$$\left(\sum_{i=0}^{p-1} G^i\right)' s(t) = v(t2) \qquad \text{Equation 4}$$

where s(t) is the periodic component, p represents a number of observed values during the predetermined time interval, G represents a time delay operator, and v(t2) represents white noise.

10. The biological information processing method according to claim 1, wherein the periodic component is represented by a substantially constant amplitude and frequency of the measured extracellular expression level of the time series data y(t), and wherein the environmental stimulus response component is represented by a change in a substantially constant average magnitude or in a substantially constant average magnitude shift of the measured extracellular expression level of the time series data y(t).

11. The biological information processing method according to claim 1, wherein treating for the predicted disease includes providing a treatment option for the predicted disease.

12. A biological information processing method comprising the steps of:
creating time-series data y(t) showing changes in a measured extracellular expression level of biological molecules in an organism;
creating baseline data b(t) by extracting from the time-series data y(t) at least one of a periodic component of the measured extracellular expression level of the time series data y(t) and an environmental stimulus response component of the measured extracellular expression level of the time series data y(t);
dividing the baseline data b(t) into a plurality of constant regions based on changes in magnitude of the baseline data over the predetermined time interval;
creating a matrix of data having a p×n matrix size, where n represents the constant regions for p types of biological molecules;
predicting onset of a disease based on a pattern of change across nodes of the matrix, the pattern determined from measured expression levels of biological molecules known to have the disease; and
treating for the predicted disease,
wherein the time-series data y(t) is expressed by the following Equation 1:

$$y(t)=s(t)+x(t)+b(t)+v(t) \qquad \text{Equation 1,}$$

where s(t) is the periodic component, x(t) is the environmental stimulus response component, b(t) is the baseline data, and v(t) is an observational error.

13. The biological information processing method according to claim 12, wherein the environmental stimulus response component includes one or more change in magnitude of the measured extracellular expression level of the time series data y(t) caused by an external environment.

14. The biological information processing method according to claim 12, wherein the periodic component is represented by a substantially constant amplitude and frequency of the measured extracellular expression level of the time series data y(t), and wherein the environmental stimulus response component is represented by a change in a substantially constant average magnitude or in a substantially constant average magnitude shift of the measured extracellular expression level of the time series data y(t).

15. The biological information processing method according to claim 12, wherein treating for the predicted disease includes providing a treatment option for the predicted disease.

16. A biological information processing method comprising the steps of:
creating time-series data y(t) showing changes in a measured extracellular expression level of biological molecules in an organism;
creating baseline data b(t) by extracting from the time-series data y(t) an environmental stimulus response component of the measured extracellular expression level of the time series data y(t);
dividing the baseline data b(t) into a plurality of constant regions based on changes in magnitude of the baseline data over the predetermined time interval;
creating a matrix of data having a p×n matrix size, where n represents the constant regions for p types of biological molecules;
predicting onset of a disease based on a pattern of change across nodes of the matrix, the pattern determined from measured expression levels of biological molecules known to have the disease; and
treating for the predicted disease,
wherein the environmental stimulus response component is formulated using the following multilinear model expressed by Equation 2:

$$x(t)=F(t)\times(t-1)+v_x(t) \qquad \text{Equation 2,}$$

where x(t) is the environmental stimulus response component, F(t) represents a conversion function of an output with respect to an environmental stimulus, and $v_x(t)$ represents a change of an environmental stimulus.

17. The biological information processing method according to claim 16, wherein the environmental stimulus response component includes one or more change in magnitude of the measured extracellular expression level of the time series data y(t) caused by an external environment.

18. The biological information processing method according to claim 16, wherein the environmental stimulus response component is represented by a change in a substantially constant average magnitude or in a substantially constant average magnitude shift of the measured extracellular expression level of the time series data y(t).

19. The biological information processing method according to claim 16, which includes measuring the extracellular expression level of biological molecules in the organism over a predetermined time interval.

20. The biological information processing method according to claim 16, wherein creating the baseline data b(t) includes extracting from the time-series data y(t) a periodic component of the measured extracellular expression level of the time series data y(t).

21. The biological information processing method according to claim 16, wherein treating for the predicted disease includes providing a treatment option for the predicted disease.

22. A biological information processing method comprising the steps of:
creating time-series data y(t) showing changes in a measured extracellular expression level of biological molecules in an organism;
creating baseline data b(t) by extracting from the time-series data y(t) at least one of a periodic component of the measured extracellular expression level of the time series data y(t) and an environmental stimulus response component of the measured extracellular expression level of the time series data y(t);

dividing the baseline data b(t) into a plurality of constant regions based on changes in magnitude of the baseline data over the predetermined time interval;

creating a matrix of data having a p×n matrix size, where n represents the constant regions for p types of biological molecules;

predicting onset of a disease based on a pattern of change across nodes of the matrix, the pattern determined from measured expression levels of biological molecules known to have the disease; and treating for the predicted disease, wherein the baseline data is expressed by the following Equation 3:

$$b(t)=H(t,t-1)b(t-1)+V(t,t-1) \quad \text{Equation 3,}$$

where b(t) is the baseline data, H(t, t−1) is an m×m matrix, and V(t, t−1) is a matrix associated with m-dimensional noise.

23. The biological information processing method according to claim 22, wherein the environmental stimulus response component includes one or more change in magnitude of the measured extracellular expression level of the time series data y(t) caused by an external environment.

24. The biological information processing method according to claim 22, wherein the periodic component is represented by a substantially constant amplitude and frequency of the measured extracellular expression level of the time series data y(t), and wherein the environmental stimulus response component is represented by a change in a substantially constant average magnitude or in a substantially constant average magnitude shift of the measured extracellular expression level of the time series data y(t).

25. The biological information processing method according to claim 22, which includes measuring the extracellular expression level of biological molecules in the organism over a predetermined time interval.

26. The biological information processing method according to claim 22, wherein treating for the predicted disease includes providing a treatment option for the predicted disease.

27. A biological information processing method comprising the steps of:

creating time-series data y(t) showing changes in a measured extracellular expression level of biological molecules in an organism;

creating baseline data b(t) by extracting from the time-series data y(t) a periodic component of the measured extracellular expression level of the time series data y(t);

dividing the baseline data b(t) into a plurality of constant regions based on changes in magnitude of the baseline data over the predetermined time interval;

creating a matrix of data having a p×n matrix size, where n represents the constant regions for p types of biological molecules;

predicting onset of a disease based on a pattern of change across nodes of the matrix, the pattern determined from measured expression levels of biological molecules known to have the disease; and treating for the predicted disease, wherein the periodic component is formulated as a seasonal adjustment model as expressed in the following Equation 4:

$$\left(\sum_{i=0}^{p-1} G^i\right)' s(t) = v(t2) \quad \text{Equation 4}$$

where s(t) is the periodic component, p represents a number of observed values during the predetermined time interval, G represents a time delay operator, and v(t2) represents white noise.

28. The biological information processing method according to claim 27, wherein creating the baseline data b(t) includes extracting from the time-series data y(t) an environmental stimulus response component of the measured extracellular expression level of the time series data y(t), wherein the environmental stimulus response component is represented by a change in a substantially constant average magnitude or in a substantially constant average magnitude shift of the measured extracellular expression level of the time series data y(t).

29. The biological information processing method according to claim 27, wherein the periodic component is represented by a substantially constant amplitude and frequency of the measured extracellular expression level of the time series data y(t).

30. The biological information processing method according to claim 27, which includes measuring the extracellular expression level of biological molecules in the organism over a predetermined time interval.

31. The biological information processing method according to claim 27, wherein treating for the predicted disease includes providing a treatment option for the predicted disease.

* * * * *